(12) United States Patent
Chu

(10) Patent No.: US 9,636,201 B2
(45) Date of Patent: May 2, 2017

(54) DELIVERY MEMBERS FOR DELIVERING AN IMPLANT INTO A BODY OF A PATIENT

(75) Inventor: Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 456 days.

(21) Appl. No.: 13/463,501

(22) Filed: May 3, 2012

(65) Prior Publication Data

US 2012/0289770 A1    Nov. 15, 2012

Related U.S. Application Data

(60) Provisional application No. 61/485,372, filed on May 12, 2011.

(51) Int. Cl.
*A61F 2/00* (2006.01)
*A61B 17/06* (2006.01)
*A61B 17/00* (2006.01)

(52) U.S. Cl.
CPC ...... *A61F 2/0045* (2013.01); *A61B 17/06166* (2013.01); *A61B 17/06109* (2013.01); *A61B 2017/00805* (2013.01); *A61B 2017/06042* (2013.01); *A61F 2220/0016* (2013.01)

(58) Field of Classification Search
CPC ........ A61F 2/08; A61F 2/0045; A61F 2/0004; A61F 2/0031; A61F 2/0036; A61F 2/0063; A61F 2017/0401; A61B 17/06166; A61B 17/06109
USPC ..................................... 600/37, 30; 606/151
See application file for complete search history.

(56) References Cited

U.S. PATENT DOCUMENTS

| | | | |
|---|---|---|---|
| 3,003,155 A | 10/1961 | Mielzynski et al. |
| 5,013,136 A | 5/1991 | Whitehead et al. |
| 5,112,344 A | 5/1992 | Petros |
| 5,197,983 A | 3/1993 | Berman et al. |
| 5,250,054 A | 10/1993 | Li |
| 5,425,740 A | 6/1995 | Hutchinson, Jr. |

(Continued)

FOREIGN PATENT DOCUMENTS

| | | |
|---|---|---|
| AU | 4092199 A | 12/1999 |
| CA | 2333121 A1 | 11/1999 |

(Continued)

OTHER PUBLICATIONS

"New Improvements in the Treatment of Female Stress Incontinence", European Association of Urologists, American Medical Systems, Mar. 2003, 34 pages.

(Continued)

*Primary Examiner* — Charles A Marmor, II
*Assistant Examiner* — Carrie R Dorna
(74) *Attorney, Agent, or Firm* — Brake Hughes Bellermann LLP

(57) ABSTRACT

In one embodiment, a medical device includes a first elongate portion and a second elongate portion. The first elongate portion defines a loop and has a first end portion and a second end portion. The first end portion is configured to be removably coupled to an implant. The second elongate portion has a first end portion and a second end portion. The first end portion of the second elongate portion is coupled to the first elongate portion. The second end portion of the second elongate portion is configured to be removably coupled to an insertion tool.

20 Claims, 16 Drawing Sheets

(56) References Cited

U.S. PATENT DOCUMENTS

| | | |
|---|---|---|
| 5,439,470 A | 8/1995 | Li |
| 5,439,474 A | 8/1995 | Li |
| 5,443,472 A | 8/1995 | Li |
| 5,449,366 A | 9/1995 | Li |
| 5,464,189 A | 11/1995 | Li |
| 5,500,000 A | 3/1996 | Feagin et al. |
| 5,520,703 A | 5/1996 | Essig et al. |
| 5,549,636 A | 8/1996 | Li |
| 5,575,805 A | 11/1996 | Li |
| 5,611,515 A | 3/1997 | Benderev et al. |
| 5,643,266 A | 7/1997 | Li |
| 5,645,589 A | 7/1997 | Li |
| 5,649,937 A | 7/1997 | Bito et al. |
| 5,690,649 A | 11/1997 | Li |
| 5,697,931 A | 12/1997 | Thompson |
| 5,702,215 A | 12/1997 | Li |
| 5,707,395 A | 1/1998 | Li |
| 5,715,942 A | 2/1998 | Li et al. |
| 5,741,300 A | 4/1998 | Li |
| 5,776,147 A | 7/1998 | Dolendo |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chalfringeon et al. |
| 5,922,026 A | 7/1999 | Chin |
| 5,935,138 A | 8/1999 | McJames, II et al. |
| 5,954,057 A | 9/1999 | Li |
| 6,022,373 A | 2/2000 | Li |
| 6,039,686 A | 3/2000 | Kovac |
| 6,039,761 A | 3/2000 | Li et al. |
| 6,042,534 A | 3/2000 | Gellman et al. |
| 6,042,582 A | 3/2000 | Ray |
| 6,042,592 A | 3/2000 | Schmitt |
| 6,096,060 A | 8/2000 | Fitts et al. |
| 6,099,538 A | 8/2000 | Moses et al. |
| 6,110,101 A | 8/2000 | Tihon et al. |
| 6,117,161 A | 9/2000 | Li et al. |
| 6,129,762 A | 10/2000 | Li |
| 6,149,669 A | 11/2000 | Li |
| 6,200,330 B1 | 3/2001 | Benderev et al. |
| 6,224,616 B1 | 5/2001 | Kugel |
| 6,273,852 B1 | 8/2001 | Lehe et al. |
| 6,355,053 B1 | 3/2002 | Li |
| 6,406,423 B1 | 6/2002 | Scetbon |
| 6,451,030 B2 | 9/2002 | Li et al. |
| 6,452,450 B1 | 9/2002 | Enriquez |
| 6,464,706 B1 | 10/2002 | Winters |
| 6,478,727 B2 | 11/2002 | Scetbon |
| 6,491,703 B1 | 12/2002 | Ulmsten |
| 6,506,190 B1 | 1/2003 | Walshe |
| 6,530,943 B1 | 3/2003 | Hoepffner et al. |
| 6,575,897 B1 | 6/2003 | Ory et al. |
| 6,582,443 B2 | 6/2003 | Cabak et al. |
| 6,592,515 B2 | 7/2003 | Thierfelder et al. |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,666,817 B2 | 12/2003 | Li |
| 6,685,629 B2 | 2/2004 | Therin |
| 6,691,711 B2 | 2/2004 | Raz et al. |
| 6,695,855 B1 | 2/2004 | Gaston |
| 6,786,861 B1 | 9/2004 | Pretorius |
| 6,808,486 B1 | 10/2004 | O'Donnell |
| 6,808,487 B2 | 10/2004 | Migliari |
| 6,852,330 B2 | 2/2005 | Bowman et al. |
| 6,884,212 B2 | 4/2005 | Thierfelder et al. |
| 6,884,428 B2 | 4/2005 | Binette et al. |
| 6,911,003 B2 | 6/2005 | Anderson et al. |
| 6,936,052 B2 | 8/2005 | Gellman et al. |
| 6,960,160 B2 | 11/2005 | Browning |
| 6,971,252 B2 | 12/2005 | Therin et al. |
| 6,986,780 B2 | 1/2006 | Rudnick et al. |
| 7,025,063 B2 | 4/2006 | Snitkin et al. |
| 7,070,556 B2 | 7/2006 | Anderson et al. |
| 7,083,568 B2 | 8/2006 | Neisz et al. |
| 7,083,637 B1 | 8/2006 | Tannhauser |
| 7,121,997 B2 | 10/2006 | Kammerer et al. |
| 7,131,944 B2 | 11/2006 | Jacquetin |
| 7,361,138 B2 | 4/2008 | Wagner et al. |
| 7,527,588 B2 | 5/2009 | Zaddem et al. |
| 7,789,821 B2 | 9/2010 | Browning |
| 7,878,969 B2 | 2/2011 | Chu et al. |
| 8,043,205 B2 | 10/2011 | MacLean |
| 8,535,216 B2 | 9/2013 | Chu et al. |
| 9,107,659 B2 | 8/2015 | MacLean |
| 9,132,002 B2 | 9/2015 | Chu et al. |
| 2001/0049467 A1 | 12/2001 | Lehe et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0083820 A1 | 7/2002 | Greenhalgh |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0133236 A1 | 9/2002 | Rousseau |
| 2002/0138025 A1 | 9/2002 | Gellman et al. |
| 2002/0147382 A1 | 10/2002 | Neisz et al. |
| 2002/0156476 A1 | 10/2002 | Wilford |
| 2002/0156487 A1 | 10/2002 | Gellman et al. |
| 2002/0161382 A1 | 10/2002 | Neisz et al. |
| 2002/0183762 A1 | 12/2002 | Anderson et al. |
| 2002/0188169 A1 | 12/2002 | Kammerer et al. |
| 2003/0004399 A1 | 1/2003 | Belson |
| 2003/0004580 A1 | 1/2003 | Sump et al. |
| 2003/0004581 A1 | 1/2003 | Rousseau |
| 2003/0065246 A1 | 4/2003 | Inman et al. |
| 2003/0075792 A1 | 4/2003 | Ruhland |
| 2003/0078468 A1 | 4/2003 | Skiba et al. |
| 2003/0078604 A1 | 4/2003 | Walshe |
| 2003/0114865 A1 | 6/2003 | Sater |
| 2003/0114866 A1 | 6/2003 | Ulmsten et al. |
| 2003/0130670 A1 | 7/2003 | Anderson et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0191480 A1 | 10/2003 | Ulmsten et al. |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0004600 A1 | 1/2004 | Yoneno et al. |
| 2004/0005353 A1 | 1/2004 | Lopez-Berestein et al. |
| 2004/0015048 A1 | 1/2004 | Neisz et al. |
| 2004/0015057 A1 | 1/2004 | Rocheleau et al. |
| 2004/0039453 A1 | 2/2004 | Anderson et al. |
| 2004/0039456 A1 | 2/2004 | Davlin et al. |
| 2004/0068159 A1 | 4/2004 | Neisz et al. |
| 2004/0087970 A1 | 5/2004 | Chu et al. |
| 2004/0097974 A1 | 5/2004 | De Leval |
| 2004/0106847 A1 | 6/2004 | Benderev |
| 2004/0133217 A1 | 7/2004 | Watschke |
| 2004/0144395 A1 | 7/2004 | Evans et al. |
| 2004/0225181 A1 | 11/2004 | Chu et al. |
| 2004/0230092 A1 | 11/2004 | Thierfelder et al. |
| 2004/0243166 A1 | 12/2004 | Odermatt et al. |
| 2004/0249240 A1 | 12/2004 | Goldmann et al. |
| 2004/0249397 A1 | 12/2004 | Delorme et al. |
| 2004/0249473 A1 | 12/2004 | Delorme et al. |
| 2004/0267088 A1 | 12/2004 | Kammerer |
| 2005/0004424 A1 | 1/2005 | Raz et al. |
| 2005/0004426 A1 | 1/2005 | Raz et al. |
| 2005/0004427 A1 | 1/2005 | Cervigni |
| 2005/0004576 A1 | 1/2005 | Benderev |
| 2005/0021086 A1 | 1/2005 | De Leval |
| 2005/0043820 A1 | 2/2005 | Browning |
| 2005/0055027 A1 | 3/2005 | Yeung et al. |
| 2005/0065395 A1 | 3/2005 | Mellier |
| 2005/0070829 A1 | 3/2005 | Therin et al. |

(56) References Cited

U.S. PATENT DOCUMENTS

| | | |
|---|---|---|
| 2005/0080317 A1 | 4/2005 | Merade |
| 2005/0107805 A1 | 5/2005 | Bouffier et al. |
| 2005/0107834 A1 | 5/2005 | Freeman et al. |
| 2005/0234460 A1 | 10/2005 | Miller |
| 2005/0245787 A1 | 11/2005 | Cox et al. |
| 2005/0250977 A1 | 11/2005 | Montpetit et al. |
| 2005/0261547 A1 | 11/2005 | Bouffier |
| 2005/0267325 A1 | 12/2005 | Bouchier et al. |
| 2005/0278037 A1 | 12/2005 | Delorme et al. |
| 2006/0041185 A1 | 2/2006 | Browning |
| 2006/0058575 A1 | 3/2006 | Zaddem |
| 2006/0058578 A1 | 3/2006 | Browning |
| 2006/0089525 A1* | 4/2006 | Mamo et al. ............... 600/37 |
| 2006/0205995 A1 | 9/2006 | Browning |
| 2007/0021649 A1* | 1/2007 | Nowlin et al. ............. 600/30 |
| 2007/0055095 A1* | 3/2007 | Chu et al. .................. 600/37 |
| 2007/0173864 A1 | 7/2007 | Chu |
| 2008/0081945 A1* | 4/2008 | Toso et al. ................. 600/37 |
| 2009/0221868 A1* | 9/2009 | Evans .............. A61F 2/0045 600/37 |
| 2010/0198003 A1* | 8/2010 | Morningstar et al. ...... 600/37 |
| 2010/0261955 A1* | 10/2010 | O'Hern et al. ............. 600/37 |
| 2011/0098526 A1 | 4/2011 | Chu et al. |
| 2011/0288368 A1* | 11/2011 | VanDeWeghe et al. .... 600/30 |
| 2011/0319704 A1* | 12/2011 | Chu ............................ 600/37 |
| 2012/0010462 A1 | 1/2012 | MacLean |
| 2013/0324790 A1 | 12/2013 | Chu et al. |
| 2015/0366647 A1 | 12/2015 | Chu et al. |

FOREIGN PATENT DOCUMENTS

| | | |
|---|---|---|
| CA | 2427882 A1 | 4/2002 |
| EP | 0632999 A1 | 1/1995 |
| EP | 0643945 A2 | 3/1995 |
| EP | 0677297 B1 | 12/2000 |
| EP | 1191902 A1 | 4/2002 |
| EP | 0774240 B1 | 3/2003 |
| EP | 1342454 A1 | 9/2003 |
| EP | 1345550 A1 | 9/2003 |
| EP | 1333776 B1 | 6/2004 |
| EP | 1324705 B1 | 8/2006 |
| EP | 1079740 B1 | 8/2007 |
| GB | 2382993 A | 6/2003 |
| WO | 95/18571 A1 | 7/1995 |
| WO | 97/13465 A1 | 4/1997 |
| WO | 97/16121 A1 | 5/1997 |
| WO | 98/35632 A1 | 8/1998 |
| WO | 99/59477 A1 | 11/1999 |
| WO | 00/40158 A2 | 7/2000 |
| WO | 00/74594 A1 | 12/2000 |
| WO | 00/74613 A1 | 12/2000 |
| WO | 01/06951 A1 | 2/2001 |
| WO | 01/45588 A2 | 6/2001 |
| WO | 01/78609 A2 | 10/2001 |
| WO | 02/02031 A1 | 1/2002 |
| WO | 02/19945 A2 | 3/2002 |
| WO | 02/26108 A2 | 4/2002 |
| WO | 02/28312 A1 | 4/2002 |
| WO | 02/30293 A1 | 4/2002 |
| WO | 0232284 A2 | 4/2002 |
| WO | 02/39890 A2 | 5/2002 |
| WO | 02/069781 A2 | 9/2002 |
| WO | 02/071953 A2 | 9/2002 |
| WO | 02/078548 A1 | 10/2002 |
| WO | 02/078568 A1 | 10/2002 |
| WO | 03/002027 A1 | 1/2003 |
| WO | 03/002029 A1 | 1/2003 |
| WO | 03/007847 A1 | 1/2003 |
| WO | 03/028584 A2 | 4/2003 |
| WO | 03/032867 A1 | 4/2003 |
| WO | 03/034939 A1 | 5/2003 |
| WO | 03/071962 A2 | 9/2003 |
| WO | 03/073960 A1 | 9/2003 |
| WO | 03/086205 A2 | 10/2003 |
| WO | 03/096928 A1 | 11/2003 |
| WO | 03/096929 A1 | 11/2003 |
| WO | 03/096930 A1 | 11/2003 |
| WO | 2004/004600 A1 | 1/2004 |
| WO | 2004/012626 A1 | 2/2004 |
| WO | 2004/016196 A2 | 2/2004 |
| WO | 2004/019786 A1 | 3/2004 |
| WO | 2004/045457 A1 | 6/2004 |
| WO | 2005/007079 A2 | 1/2005 |
| WO | 2005/094721 A1 | 10/2005 |
| WO | 2005/112842 A1 | 12/2005 |
| WO | 2005/122721 A2 | 12/2005 |
| WO | 2005/122954 A1 | 12/2005 |

OTHER PUBLICATIONS

"The Confident approach to curing incontinence", Monarch Subfascial hammock, American Medical Systems, 5 pages.

Kovac, et al., "Pubic Bone Suburethral Stabilization Sling for Recurrent Urinary Incontinence", Obstetrics & Gynecology, vol. 89, No. 4, Apr. 1997, pp. 493-642. Retrieved from: http://journals.lww.com/greenjournal/Abstract/1997/04000/Pubic_Bone.

Palma et al., "SAFYRE: A Readjustable Minimally Invasive Sling for Female Urinary Stress Incontinence", SafyrenTM, International Journal of the Brazilian Society of Urology, vol. 29 No. 4, 2003, pp. 353-359.

Siegel, A. L., "Vaginal Mesh Extrusion Associated with use of Mentor Transobturator Sling", Elsevier, Inc., Adult Urology, 2005, pp. 995-999.

Dargent et al., "Insertion of a sub urethral sling through the obturating membrane in the treatment of female urinary incontinence", Gynécol Obstét Fertil, vol. 30, 2002, pp. 576-582.

Dargent et al., "Pose d'un ruban sous uretral oblique par voie obturatrice dans le traitement de l'incontinence urinaire feminine", Gynécol Obstét Fertil, vol. 30, 2002, 1 page.

De Leval, J., "Novel Surgical Technique for the Treatment of Female Stress Urinary Incontinence: Transobturator Vaginal Tape Inside-Out", European Urology vol. 44, 2003, pp. 724-730.

Delorme et al., "Transobturator Tape (Uratape®): A New Minimally-Invasive Procedure to Treat Female Urinary Incontinence", European Urology 45, 2004, pp. 203-207.

Delorme, E., "The transobdurator band: a minimmaly invasive procedure for treatment of urinary stress incontinence in women", Progress in Urology, vol. 11, 2001, pp. 1306-1313.

Hermieu et al., "Les bandelettes sous-urétrales synthétiques dans le traitement de l'incontinence urinaire d'effort féminine", Progrés en Urologie, vol. 13, 2003, pp. 636-647.

Ingelman-Sundberg et al., "Surgical Treatment of Female Urinary Stress Incontinence", Contr. Gynec Obstet, vol. 10, 1983, pp. 51-69.

Nickel, R. F., "Transpelvic Sling Urethroplasty with and without Colpususpension for the Treatment of Complicated Urinary Incontinence in Bitches", Third Annual Scientific meeting (ECVS), Riccione, Jun. 23-26, 1994.

Office Action for European Patent Application No. 06788512.9, mailed on Mar. 9, 2011, 4 pages.

Non-Final Office Action for U.S. Appl. No. 11/493,148, mailed Mar. 25, 2010, 14 pages.

Notice of Allowance for U.S. Appl. No. 11/493,148, mailed on Sep. 30, 2010, 6 pages.

Non-Final Office Action for U.S. Appl. No. 12/983,589, mailed Jan. 31, 2012, 12 pages.

Final Office Action for U.S. Appl. No. 12/983,589, mailed on Jun. 6, 2012, 13 pages.

Non-Final Office Action for U.S. Appl. No. 12/983,589, mailed Oct. 17, 2012, 10 pages.

Final Office Action for U.S. Appl. No. 12/983,589, mailed on Feb. 13, 2013, 11 pages.

Notice of Allowance for U.S. Appl. No. 12/983,589, mailed on May 13, 2013, 10 pages.

Non-Final Office Action for U.S. Appl. No. 13/242,821, mailed on Jun. 3, 2013, 14 pages.

Final Office Action for U.S. Appl. No. 13/242,821, mailed Nov. 20, 2013, 12 pages.

(56) References Cited

OTHER PUBLICATIONS

Non-Final Office Action for U.S. Appl. No. 13/242,821, mailed on Mar. 7, 2014, 11 pages.
Final Office Action for U.S. Appl. No. 13/242,821, mailed on Jun. 18, 2014, 10 pages.
Non-Final Office Action for U.S. Appl. No. 13/964,685, mailed on Nov. 26, 2013, 12 pages.
Final Office Action for U.S. Appl. No. 13/964,685, mailed on Apr. 25, 2014, 15 pages.
Non Final Office Action for U.S. Appl. No. 13/964,685, mailed on Jul. 18, 2014, 10 pages.
Notice of Allowance for U.S. Appl. No. 13/242,821, mailed on Apr. 15, 2015, 7 pages.
Notice of Allowance for U.S. Appl. No. 13/964,685, mailed on May 8, 2015, 10 pages.

\* cited by examiner

DELIVERY MEMBERS FOR DELIVERING AN IMPLANT INTO A BODY OF A PATIENT

CROSS-REFERENCE TO RELATED APPLICATION

This application is a Nonprovisional of, and claims priority to, U.S. Patent Application No. 61/485,372, filed May 12, 2011, entitled "DELIVERY MEMBERS FOR DELIVERING AN IMPLANT INTO A BODY OF A PATIENT", which is incorporated by reference herein in its entirety.

TECHNICAL FIELD

This disclosure relates generally to medical devices and more particularly to implants configured to provide support within a pelvic region of a patient and delivery members for delivering such implants into the pelvic region of the patient.

BACKGROUND

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Known implants are configured to provide support to a patient's body to treat stress urinary incontinence. Some known implants require that a single bodily incision be made and are positioned or tensioned by controlling how far into the tissue the end portions are deposited or pushed into the anchoring tissue. Such known implants, however, can be difficult to correctly place and tension within the body of the patient.

Some known implants require that entrance and exit incisions be used to place the implant within the body of the patient. The tension within the body of some such implants may be adjusted at a time after the procedure to place the implant within the body has been completed. Some of these implants make use of sutures that are bio-resorbable so that the sutures will not be a long term irritant to the body of the patient. Such bio-resorbable sutures, however, can be expensive and time consuming to manufacture and package. Some of these implants include sutures that are not bio-resorbable and are configured to remain within the body of the patient. These sutures may cause pain and/or infection. For example, in some devices, the sutures remain extended through the obturator foramen and can be painful to the patient.

Thus, it would be desirable to provide an implant that facilitates the positioning and tensioning within the body of the patient at a time after the procedure to place the implant within the body has been completed. Additionally, it is desirable to provide an implant that allows the suture to be removed from the implant after the implant tension has been appropriately set.

SUMMARY

In one embodiment, a medical device includes a first elongate portion and a second elongate portion. The first elongate portion defines a loop and has a first end portion and a second end portion. The first end portion is configured to be removably coupled to an implant. The second elongate portion has a first end portion and a second end portion. The first end portion of the second elongate portion is coupled to the first elongate portion. The second end portion of the second elongate portion is configured to be removably coupled to an insertion tool.

DETAILED DESCRIPTION

The devices and methods described herein are generally directed to implants and the delivery and placement of such implants within a body of a patient. In some embodiments, the devices described herein are directed to implants and the delivery and placement of such implants within a pelvic region (also referred to herein as "pelvis") of a patient. The devices and implants described herein may be used with a female patient as well as a male patient.

Various embodiments of implants are described herein. An implant can be delivered to a pelvic region of a patient using a variety of different delivery tools, only some examples of which are described herein.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a sleeve assembly or dilator device as described herein refers to the end or portion of the device that is first inserted into a body of a patient during a medical procedure. The proximal end or portion is the end or portion of the device that is inserted into a body of the patient after the distal end or distal portion. The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that is inserted into the body after the leading end.

Figure 1:
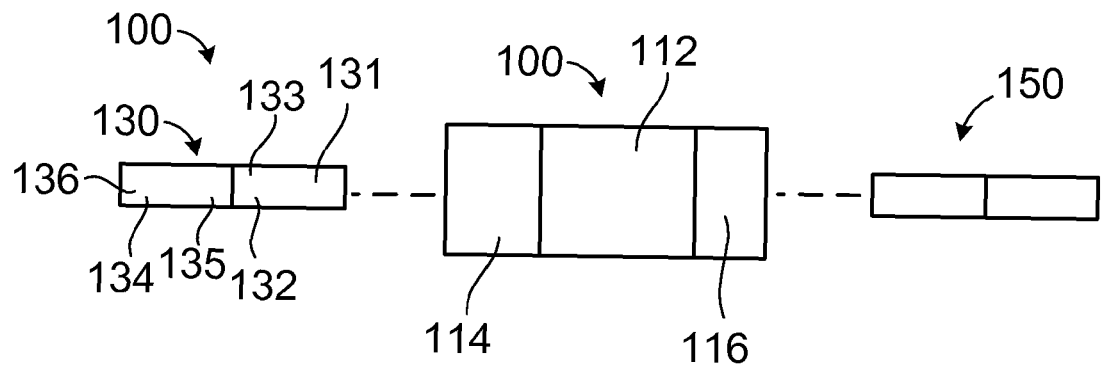
FIG. 1 is a schematic illustration of a medical device according to an embodiment of the invention.

FIG. 1 is a schematic illustration of an apparatus 100 according to an embodiment of the invention. The apparatus 100 includes an implant 110, a first delivery member 130, and a second delivery member 150. The implant 110 has a support portion 112, a first end portion 114, and a second end portion 116. The support portion 112 is disposed between the first end portion 114 and the second end portion 116.

The implant 110 is configured to be disposed in a body of a patient. The support portion 112 is configured to provide support to a portion of the body of the patient. For example, in some embodiments, the support portion 112 is configured to be placed or disposed adjacent a bladder or a bladder neck of a patient and to provide support to the bladder or bladder neck of the patient. Although many of the procedures described herein are focused on placing the implant within a body of a female patient, it should be understood that the devices and methods described herein may be used in connection with a male patient.

In some embodiments, the first end portion 114 and the second end portion 116 are configured to help support or retain the implant in place within the body of the patient. For example, in some embodiments, the first end portion 114 and the second end portion 116 are configured to be disposed within bodily tissue of the patient. In some embodiments, the first end portion 114 and the second end portion 116 are configured to be coupled to such bodily tissue to help secure the implant 110 in place within the body of the patient.

In some embodiments, the first end portion 114 and the second end portion 116 can be of any shape or size suitable for extending between the support member 112 and the bodily tissue and coupling to the bodily tissue. Additionally, the implant 110 may include additional arm members or end portions that are configured to couple to bodily tissue to help secure the implant 110 in place within the body of the patient.

In some embodiments, the first end portion 114 and the second end portion 116 are configured to be disposed within and coupled to an obturator membrane of the patient or other pelvic tissue of the patient. In other embodiments, the first end portion 114 and the second end portion 116 are configured to be coupled to other bodily tissue.

In some embodiments, the first end portion 114 and the second end portion 116 include tangs or tanged portions configured to help anchor the end portions 114 and 116 within the bodily tissue of the patient. The terms "tanged" or "tangs" as used herein mean roughened or jagged edges or areas, such as can result from cutting a woven or knit mesh material. In other embodiments, the end portions 114 and 116 include barbs, dimples and/or other protrusions configured to engage the bodily tissue of the patient to help retain the implant 110 in place within the body of the patient. In other embodiments, other mechanisms may be used to couple the end portions 114 and 116 to the bodily tissue.

The implant 110 can be formed with a mesh material to allow tissue in-growth to the implant 110 after implantation within the body of the patient. For example, some or all of the implant 110 can be formed with a mesh material as described in U.S. Patent Pub. 2005/0038452 A1 to Chu, the entirety of which is hereby incorporated by reference. In some embodiments, some or all of an implant 110 can be formed with the Advantage™ Mesh or the Polyform™ Synthetic Mesh material each provided by Boston Scientific Corporation. In some embodiments, the implant 110 is formed of a polypropylene mesh.

The implant 110 can be monolithically formed or alternatively, the implant 110 can be formed with multiple different materials and/or can include multiple different components or portions coupled together. In some embodiments, the implant can be formed with a combination of materials including synthetic and biological materials. For example, the support member 112 can be formed with a first biocompatible material and the end portions 114 and 116 can be formed with a second biocompatible material different than the first material. In other embodiments, the support member 112 is formed with a biological material, and the end portions 114 and 116 are formed with a synthetic material. In some embodiments, the end portions 114 and 116 and the support member 112 have a different weave, pitch, texture, color, and/or pattern from each other.

In some embodiments, the end portions 114 and 116 are formed monolithically with the support member 112. In other embodiments, the end portions 114 and 116 are formed separate from the support member 112 and can be coupled to the support member 112. In such embodiments, the end portions 114 and 116 and the support member 112 can be coupled in an abutting relationship, an overlapping relationship, or can be bridged. The end portions 114 and 116 can be coupled to the support member 112 by, for example, heat bonding, gluing, using fasteners, and/or sewing. In some embodiments, an arm member can include a heat seal along its length or a portion of its length to help prevent or reduce stretching of the arm member.

The first delivery member 130 and the second delivery member 150 may be structurally and functionally similar. Accordingly, only the first delivery member 130 will be described in detail.

The first delivery member 130 includes a first elongate portion 132 and a second elongate portion 134. The first elongate portion 132 is coupled to the second elongate portion 134. In some embodiments, the first elongate portion 132 includes a first end portion 131 and a second end portion 133 and the second elongate portion includes a first end portion 135 and a second end portion 136. As will be discussed in more detail below, the first end portion 131 of the first elongate portion 132 is configured to be removably coupled to the implant 110. The second end portion 133 of the first elongate portion 132 is coupled to the first end portion 135 of the second elongate portion 134. As will be discussed in more detail below, the second end portion 136 of the second elongate portion 134 is configured to be removably coupled to a delivery tool.

In some embodiments, the first elongate portion 132 and the second elongate portion 134 are unitarily or monolithically formed. In other embodiments, the first elongate portion 132 and the second elongate portion 134 are separate items and are coupled together. For example, the first elongate portion 132 may coupled to the second elongate portion 134 via a mechanical means, such as tying, or a chemical means, such as an adhesive. In some embodiments, the first elongate portion 132 is coupled to the second elongate portion 134 via an intermediate member, such as a coupler or a dilator.

The first elongate portion 132 is configured to be removably coupled to the implant 110. For example, in some embodiments, the first end portion 131 of the first elongate portion 132 is configured to be removably coupled to the first end portion 114 of the implant 110. Specifically, in some embodiments, the first elongate portion 132 is slidably coupled to the implant 110 and is configured to be removed from or decoupled from the implant 110 while the implant 110 is disposed within a body of a patient.

In some embodiments, the implant 110 includes a coupling member configured to facilitate the coupling of the first elongate portion 132 of the first delivery member 130 to the implant 110. In other embodiments, another mechanism may be used to removably couple the first elongate member 132 of the first delivery member 130 to the implant 110.

In some embodiments, the first elongate portion 132 of the first delivery member 130 forms, defines, and/or includes a loop or a loop portion. In some embodiments, the loop portion is configured to be removably coupled to the implant 110.

The second elongate portion 134 of the first delivery member 130 is configured to be removably coupled to a delivery tool, such as a needle or other type of delivery tool. Specifically, in some embodiments, the second end portion 136 of the second elongate portion 134 is configured to be removably coupled to the delivery tool. For example, the second elongate portion 134 may be coupled to the delivery tool during the placement of the delivery member 130 within the body of the patient. The second elongate portion 134 may then be removed from the delivery tool (after the delivery member 130 has been placed within the body of the patient). In some embodiments, the second elongate portion 134 defines, forms, or includes a loop or loop portion.

The first delivery member 130 may be formed of a strand of material or fiber or multiple strands of material or fiber. In some embodiments, the first delivery member 130 is formed of a biocompatible material such as a polymer, a metal, bovine materials, cadaveric materials or other materials. In some embodiments, the first delivery member 130 is formed of an absorbable material. In some embodiments, the first delivery member 130 includes a coating. In some embodiments, the fiber of the first delivery member 130 is in the form of a filament, a leader, a thread, a rope, a strand, or a suture. The fiber can be braided or be a monofilament. The fiber can have any cross-sectional shape, such as round, square, rectangle, or oval.

In some embodiments, the first delivery member 130 is formed of a material that is configured to absorb fluids or medications such as an anesthetic. In such embodiments, the medication or anesthetic may be released into the body of the patient during or after the procedure to place the implant 110 within the body.

In some embodiments, the loops formed by the portions 132 and 134 of the first delivery member 130 are formed by joining ends of the fiber or filament. In other embodiments, the loops are monolithically formed.

In some embodiments, the first portion 132 of the first delivery member 130 and the second portion 134 of the first delivery member 130 are formed of the same material. In other embodiments, the first portion 132 of the first delivery member 130 and the second portion 134 of the first delivery member 130 are formed of different materials.

As will be described in more detail below, in use, the first delivery member 130 and the second delivery member 150 may be inserted into a body of a patient such that a portion of each to the member is disposed within the body of the patient and another portion of each member extends from the body of the patient. In some embodiments, the delivery member 130 and 150 are inserted into the body of the patient using a delivery tool, such as a delivery device or needle (such as a Capio® device or an Obtryx™ device as sold by Boston Scientific Corporation). For example, the delivery tool may include a coupling portion configured to removably couple the delivery members 130 and 150 to the delivery tool. In some embodiments, the delivery tool includes a tissue piercing portion and a handle configured to be handled by a physician to maneuver the delivery tool and implant into and through the body of the patient.

In some embodiments, the delivery tool may be used to deliver the delivery members 130 and 150 into a pelvic region of a patient. Once the delivery members 130 and 150 are placed within the body of the patient, the delivery members 130 and 150 may be coupled to the implant 110. The deliver members 130 and 150 may then be used (moved with respect to the body of the patient) to advance or dispose the implant 110 within the body of the patient.

The delivery member 130 and 150 may be used to place or adjust the tension of the implant 110 within the body of the patient at the time of the procedure or at a time after the procedure to place the implant within the body. For example, in some embodiments, the delivery members 130 and 150 may be used to adjust the tension of the implant 110 within the body of the patient a few hours or a few days after the procedure to place the implant within the body of the patient.

Once the implant 110 is correctly placed and tensioned within the body of the patient, the delivery members 130 and 150 may be decoupled from the implant 110 and removed from the body. In some embodiments, the delivery members 130 and 150 are decoupled from the implant 110 while the implant is entirely disposed within the body of the patient. In some embodiments, the delivery members 130 and 150 are decoupled from the implant 110 while the locations at which the delivery members 130 and 150 are coupled to the implant 110 are disposed within the body of the patient. In some embodiments, the delivery members 130 and 150 are decoupled from the implant 110 while the implant 110 is entirely disposed within the body of the patient.

Figure 2A:
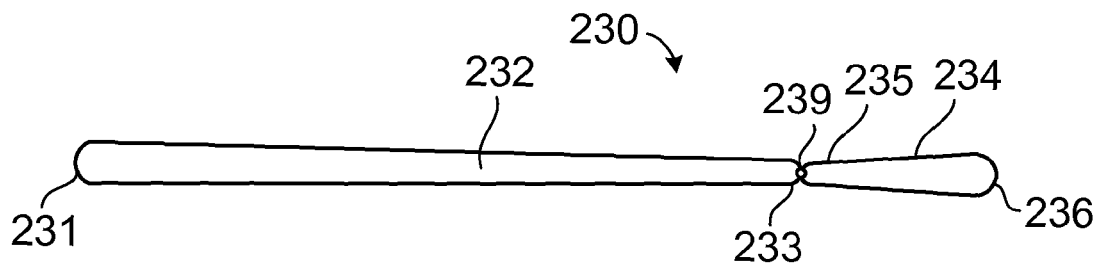
FIGS. 2A and 2B illustrate a delivery member according to an embodiment of the invention.
Figure 2B:
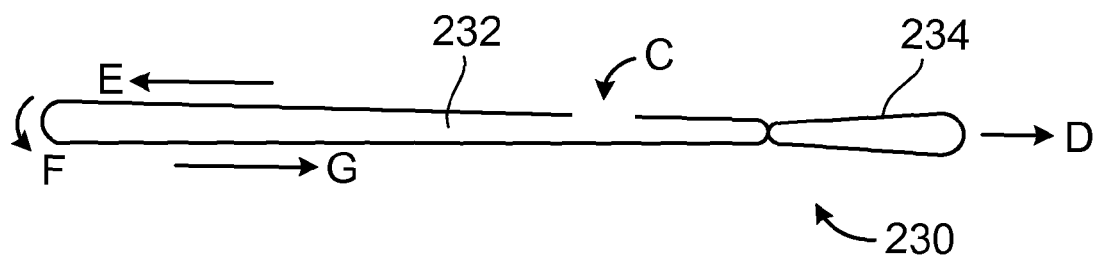

FIGS. 2A and 2B illustrate a delivery member 230 according to an embodiment of the invention. The delivery member 230 includes a first elongate portion 232 and a second elongate portion 234. The first elongate portion 232 is coupled to the second elongate portion 234. In some embodiments, the first elongate portion 232 is longer than the second elongate portion 234. In other embodiments, the elongate portions 232 and 234 are the same length. In yet further embodiments, the second elongate portion 234 is longer than the first elongate portion 232.

The first elongate portion 232 includes a first end portion 231 and a second end portion 233 and the second elongate portion 234 includes a first end portion 235 and a second end portion 236. The first end portion 231 of the first elongate portion 232 is configured to be removably coupled to an implant such as implant 210 (which will be described in more detail below). The second end portion 233 of the first elongate portion 232 is coupled via a knot 239 to the first end portion 235 of the second elongate portion 234. The second end portion 236 of the second elongate portion 234 is configured to be removably coupled to a delivery tool.

In the illustrated embodiment, the first elongate portion 232 and the second elongate portion 234 are unitarily or monolithically formed. The first elongate portion 232 and the second elongate portion 234 each defined a loop. The first elongate portion 232 and the second elongate portion 234 are separated and coupled to each other via the knot 239.

The first elongate portion 232 is configured to be removably coupled to the implant 210. As will be described in more detail below, in the illustrated embodiment, the first end portion 231 of the first elongate portion 232 is configured to engage a coupling member 220 of the implant 210 to removably couple the first elongate portion 232 to the implant 210.

The second elongate portion 234 of the delivery member 230 is configured to be removably coupled to a delivery tool, such as a needle or other type of delivery tool. Specifically, in some embodiments, the second end portion 236 of the second elongate portion 234 is configured to be removably coupled to the delivery tool. For example, the second elongate portion 234 may be coupled to the delivery tool during the placement of the delivery member 230 within the body of the patient. The second elongate portion 234 may then be removed from the delivery tool (after the delivery member 230 has been placed within the body of the patient). In the illustrated embodiment, the second elongate portion 234 defines, forms, or includes a loop or loop portion.

The delivery member 230 may be formed of a strand of material or fiber or multiple strands of material or fiber. In some embodiments, the delivery member 230 is formed of a biocompatible material such as a polymer, a metal, bovine materials, cadaveric materials or other materials. In some embodiments, the delivery member 230 is formed of an absorbable material. In some embodiments, the delivery member 230 includes a coating. In some embodiments, the fiber of the delivery member 230 is in the form of a filament, a leader, a thread, a rope, a strand, or a suture. The fiber can be braided or be a monofilament. The fiber can have any cross-sectional shape, such as round, square, rectangle, or oval.

In some embodiments, the delivery member 230 is formed of a material that is configured to absorb fluids or medications such as an anesthetic. In such embodiment, the medication or anesthetic may be released into the body of the patient during or after the procedure to place the implant 210 within the body.

As illustrated in FIG. 2B, a portion of the loop of the first elongate portion 232 may be cut. For example, the loop may be cut at location C. Accordingly, in use, once the implant 210 has been correctly placed and tensioned within the body, and while the implant 210 is disposed within the body of the patient, the loop may be cut at location C (which may be disposed outside of the body). The second elongate portion 234 may then be moved in a direction away from the body of the patient, such as in the direction of arrow D. The cut portion of the loop will then follow the direction of arrows E, F, and G to decouple from the implant 210 and exit the body of the patient.

Figure 3A:
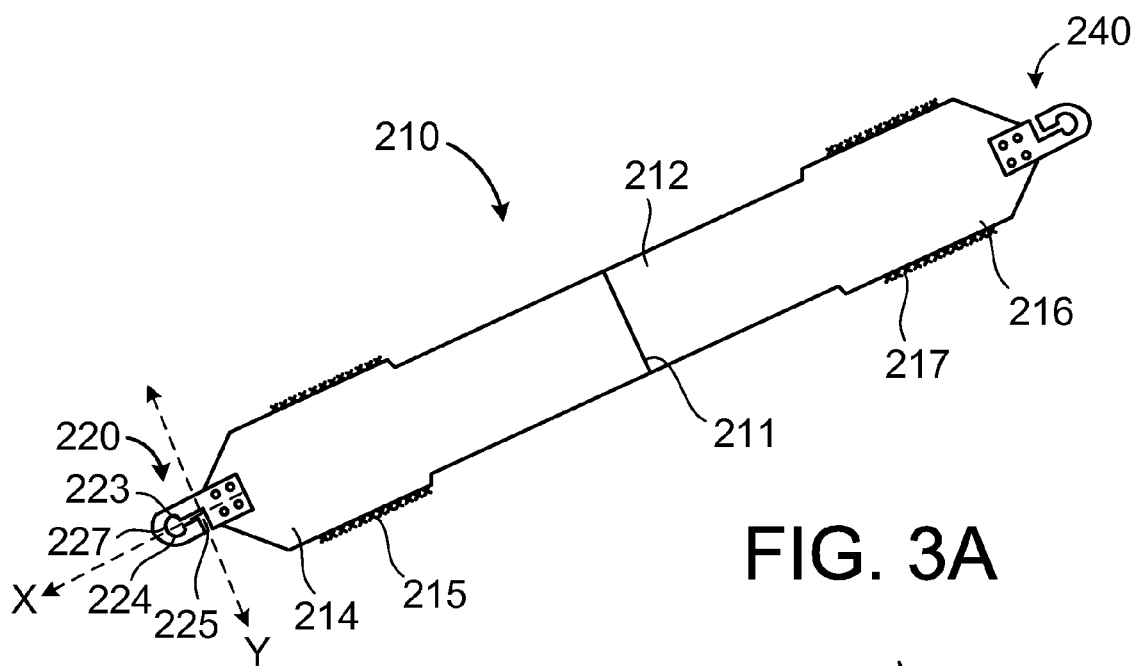
FIG. 3A is a top view of an implant according to an embodiment of the invention.

FIG. 3A illustrates an implant 210 according to an embodiment of the invention. The implant 210 is configured to be disposed in a body of a patient and includes a support portion 212 and end portions 214 and 216. The support portion 212 is configured to provide support to a portion of the body of the patient. For example, in some embodiments, the support portion 212 is configured to be placed or disposed adjacent a bladder or a bladder neck of a patient and to provide support to the bladder or bladder neck of the patient.

The first end portion 214 and the second end portion 216 are configured to be disposed within bodily tissue of the patient. In some embodiments, the first end portion 214 and the second end portion 216 are configured to be coupled to such bodily tissue to help secure the implant 210 in place within the body of the patient.

The first end portion 214 and the second end portion 216 can be of any shape or size suitable for extending between the support member 212 and the bodily tissue and coupling to the bodily tissue. Additionally, the implant 210 may include additional arm members or end portions that are configured to couple to bodily tissue to help secure the implant 210 in place within the body of the patient.

In the illustrated embodiment, the first end portion 214 and the second end portion 216 are configured to be disposed within and coupled to bodily tissue. Specifically, the first end portion 214 and the second end portion 216 are configured to be disposed within and coupled to pelvic tissue, such as an obturator membrane, an obturator muscle, or other pelvic tissue.

In the illustrated embodiment, the implant 210 includes tanged portions 215 and 217. The tanged portions 215 and 217 configured to help anchor the end portions 214 and 216 within the bodily tissue of the patient.

In the illustrated embodiment, the implant 210 is an incontinence sling and is about 10 cm in length. In other embodiments, the implant is of a length greater than 10 cm. In yet further embodiments, the implant is of a length less than 10 cm.

In the illustrated embodiment, the implant 210 includes a center line 211. The center line 211 is a marking, such an ink marking, that identifies the center of the implant 210. The center line 211 may facilitate the proper placement of the implant within the body of the patient.

In the illustrated embodiment, the implant 210 is tapered at both ends. Specifically, the width of the implant 210 gets smaller towards the end portions 214 and 216 of the implant 210. In other embodiments, the implant does not include tapered portions.

In the illustrated embodiment, the implant 210 includes a first coupling member 220 and a second coupling member 240. The first coupling member 220 and the second coupling member 225 are structurally and functionally similar. Accordingly, only the first coupling member 220 will be discussed in detail.

The first coupling member 220 is coupled to the first end portion 214 of the implant 210. The first coupling member 220 is configured to removably couple the delivery member, such as delivery member 230 to the implant 210. In the illustrated embodiment, the first coupling member 220 includes or defines a slot 224.

In some embodiments, the coupling member 220 is formed of two pieces that are coupled together to sandwich the implant (i.e., the implant is disposed between the two pieces of the coupling member 220). In other embodiments, the coupling member is molded to (such as insert molded) to the implant 210.

In some embodiments, the coupling member 220 has an oval, flat, or triangular shape. In other embodiments, the coupling member 220 has a different shape. In some embodiments, the coupling member 220 includes anchors or barbs that are configured to help couple the implant 210 in place within the body of the patient.

In the illustrated embodiment, the slot 224 is "L" shaped. Specifically, the slot includes a first portion 223 and a second portion 225. The first portion 223 of the slot 224 extends along a first axis X. The second portion 225 of the slot 224 extends along a second axis Y. The first axis X is angled with respect to the second axis Y. In other words, the first axis X is not parallel to the second axis Y. Specifically, in the illustrated embodiment, the first axis X is perpendicular to the second axis Y.

The slot 224 is configured to receive the first elongate portion 232 of the delivery member 230. Specifically, the loop portion of the first elongate portion 232 (or an end portion 231 of the first elongate portion 232) may be slid or positioned within the slot 224. In the illustrated embodiment, the slot 224 includes an end portion 227 that is wider or larger than the mid-portion of the slot 224. Accordingly, the first elongate portion 232 may be moved within the slot 224 to the end portion 227. As the end portion 227 is wider than the mid-portion of the slot 224, in some embodiments, the first elongate portion 232 may snap-fit into place within the end portion 227 of the slot 224. In other words, the first elongate portion 232 tends to remain within the end portion 227 of the slot 224 once it is placed therein. For example, in some embodiments, the first elongate portion 232 is frictionally fit within the end portion 227 of the slot 224.

Once the first elongate portion 232 is coupled to the implant 210, the implant may be moved by moving the elongate portion 232 with respect to the body of the patient. The loop portion of the first elongate portion 232 is slidably or movably disposed within the slot 224. Thus, to remove or decouple the first elongate portion 232 from the implant 210, the loop portion of the first elongate portion 232 can be cut and the first elongate portion 232 can be pulled or moved through the slot 224.

Figure 3B:
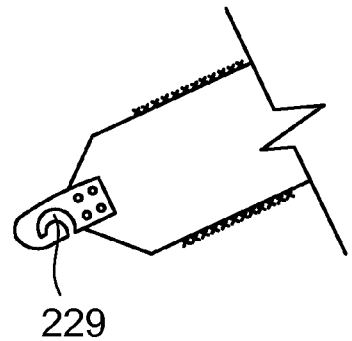
FIG. 3B is a top view of a portion of an implant according to another embodiment of the invention.

FIG. 3B illustrates an alternative shape of the slot. In this embodiment, the coupling member defines a curved or comma shaped slot 229. In other embodiment, the coupling member defines a slot that has a different shape, such as a T shape, an I shape, or an H shape.

Figure 4:
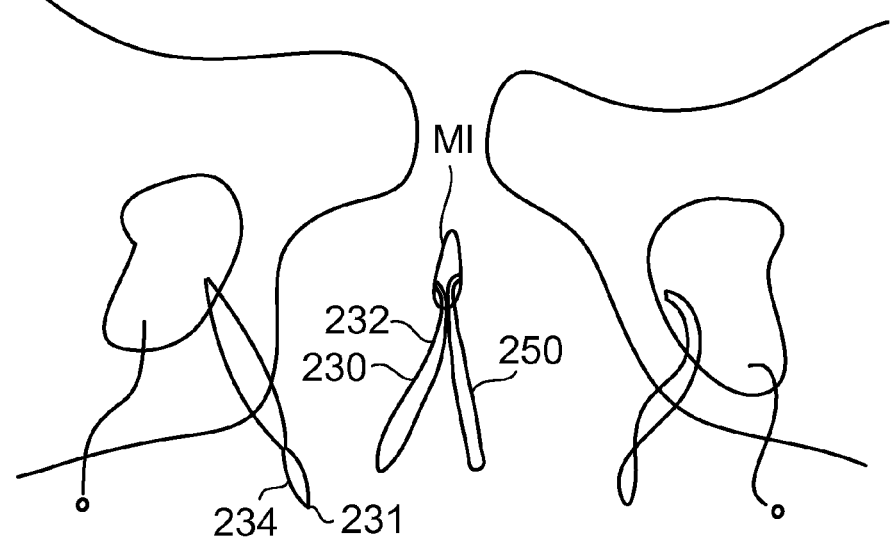
FIGS. 4-9 illustrate various steps of placing a medical device within a body of a patient.

FIGS. 4-9 schematically illustrate the placement of an implant within a body of a patient. As illustrated in FIG. 4, the delivery members 230 and 250 may be placed within the body of the patient such that a portion of each of the delivery members 230 and 250 is disposed outside of the body of the patient while another portion of each of the delivery members 230 and 250 is disposed within the body of the patient.

In the illustrated embodiment, the delivery members 230 and 250 are disposed within the body of the patient such that the delivery members 230 and 250 extend from a location outside of the body of the patient, through the midline incision MI (vaginal incision), through an obturator foramen O, and out a skin incision proximate the obturator foramen (a location outside of the body of the patient). In other embodiments, the delivery members 230 and 250 may extend into and through different portions of the body of the patient. In some embodiments, the delivery members 230 and 250 extend from another incision, such as an anterior vaginal incision or a posterior vaginal incision.

The delivery members 230 and 250 may be placed within the body of the patient using a delivery tool. For example, an end portion (such as end portion 236 of second elongate portion 234 of the delivery member 230) of the delivery members 230 and 250 may be coupled to a delivery tool, such as a delivery needle. The delivery tool and the delivery member may then be inserted and placed within the body of the patient. For example, a delivery tool may be removably coupled to end portion 236 of the second elongate portion 234 of the first delivery member 230. The delivery tool may then be inserted into the body of the patient (such as through the vaginal midline incision MI). The delivery tool can then be advanced through the obturator foramen and out an adjacent skin incision. As the delivery tool is advanced, the first delivery member 230 is pulled into place within the body of the patient. Once the end of the delivery tool and the end 236 of the delivery member 230 extend from the skin incision, the delivery member 230 may be removed from or decoupled from the delivery tool. The delivery tool may then be retracted from the body of the patient leaving the delivery member 230 in place within the body of the patient. Using a similar process, the delivery member 250 may be placed on the contra-lateral side of the patient.

Figure 5A:
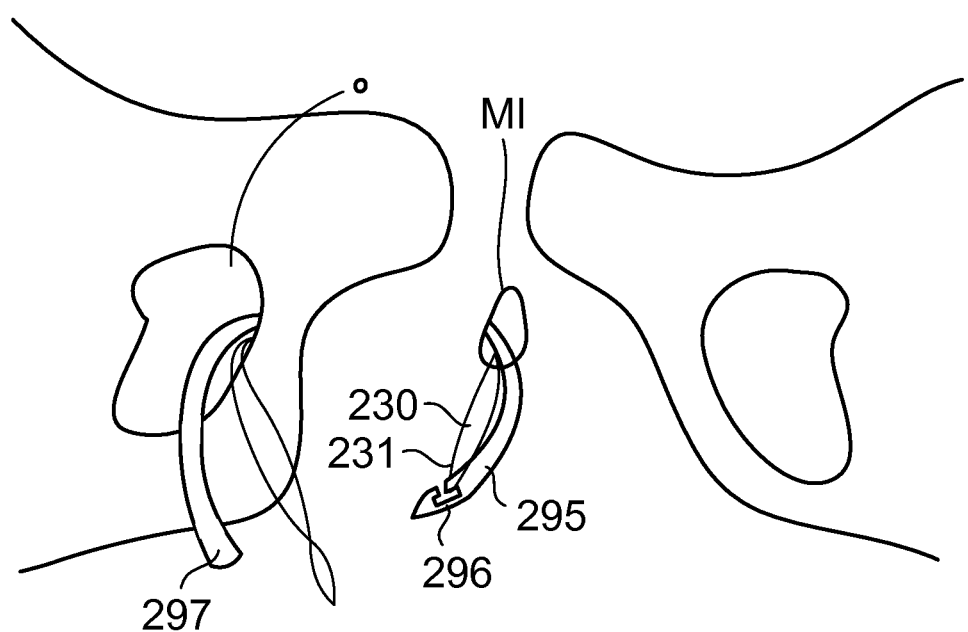
Figure 5B:
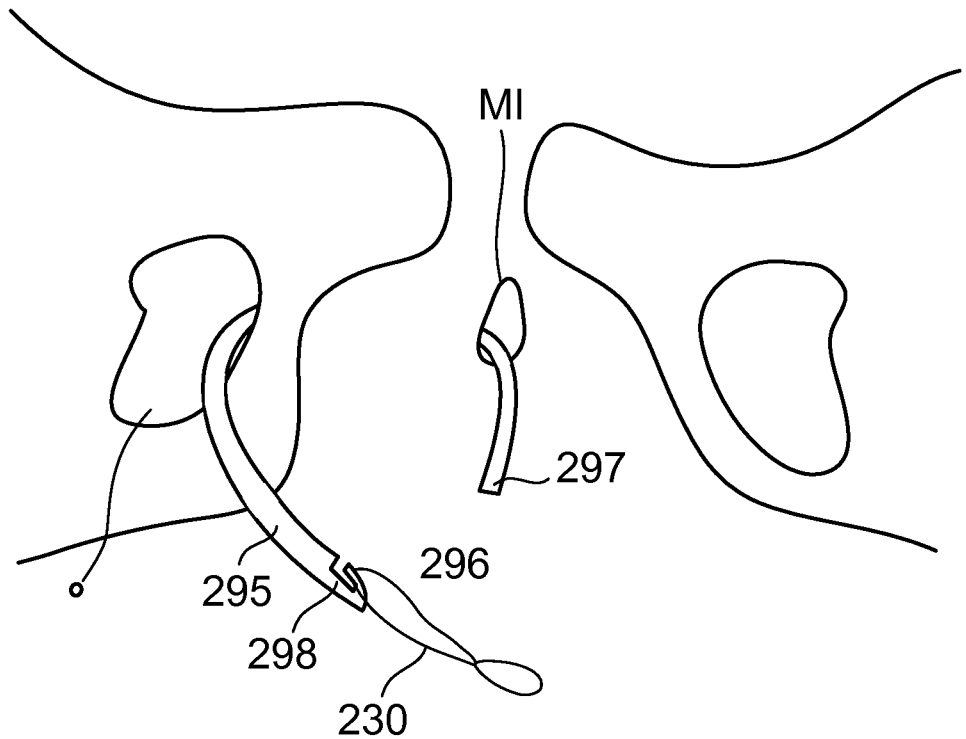

FIGS. 5A and 5B illustrate other methods for placing the delivery members 230 and 250 into the body of the patient. FIG. 5A illustrates an outside-in approach. In this embodiment, a delivery tool 295 is coupled to an end portion 236 of the delivery member 230. In some embodiments, the delivery tool 295 includes a 16 or a 14 gauge needle. In other embodiments, the delivery tool 295 includes a needle of another size.

The delivery tool 295 includes a T shaped slot 296 that is configured to facilitate the coupling and placement of the delivery member 230 within the body of the patient. Once the delivery member 230 is coupled to the delivery tool 295, using the handle portion 297 of the delivery tool, a physician may direct the delivery tool 295 into the body of a patient through an external skin incision, through the obturator foramen O, and through the vaginal midline incision MI. The delivery member 230 may then be decoupled or removed from the delivery tool 295 and the delivery tool 295 may be retracted from the body of the patient leaving the delivery member 230 within the body of the patient with its end portions extending from the body.

FIG. 5B illustrates an inside-out approach to placing the delivery member 230 within the body of the patient. In this embodiment, the delivery tool 295 is passed through the vaginal midline incision MI, through the obturator O, and out a skin incision. The delivery member 230 may then be coupled to the delivery tool 295. In this embodiment, the delivery tool includes an L shaped slot 298 to facilitate the coupling and placement of the delivery member 230. The delivery tool 295 may then be retracted to pull the delivery member 230 into place within the body of the patient. The L shaped slot 298 allows the delivery tool 295 to "pull" the delivery member 230 into place but would not allow the delivery tool 295 to "push" or "carry" the delivery member 230 into place.

Figure 6:
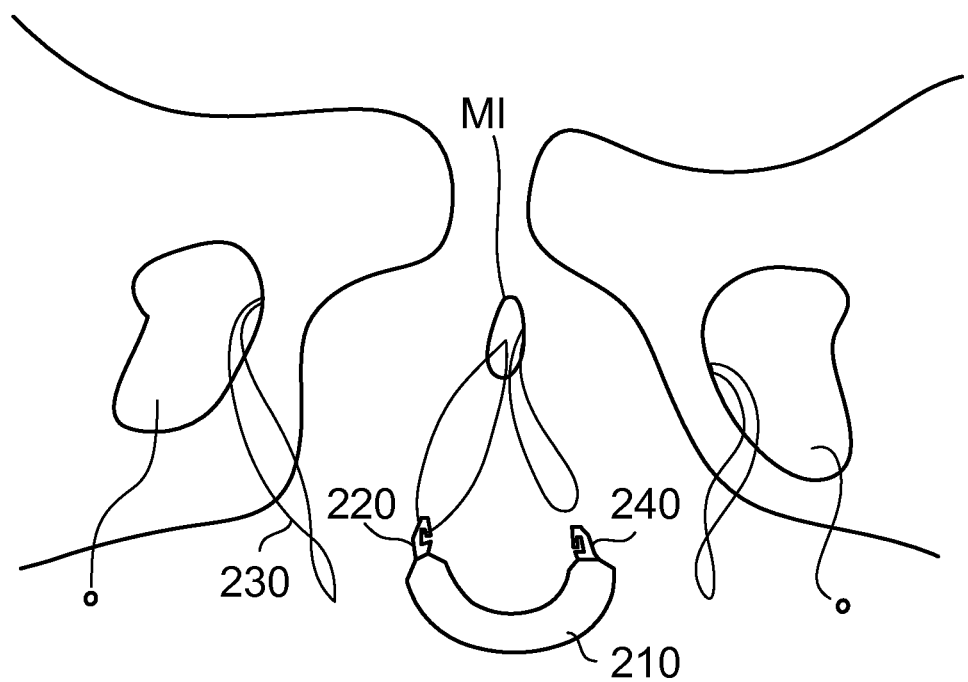

As illustrated in FIG. 6, once the delivery members 230 and 250 are placed within the body of the patient such that one portion of each of the delivery member 230 and 250 are disposed outside of the body of the patient and another portion of each of the delivery members 230 and 250 are disposed within the body of the patient, the implant 210 may be coupled to the portions of the delivery members 230 and 250 that extend from the body of the patient. Specifically, in the illustrated embodiment, both ends of each of the delivery members 230 and 250 extend from the body of the patient. In this embodiment, the implant 210 is coupled to the end portions of the delivery members 230 and 250 that are located proximal the vaginal midline incision MI. In the illustrated embodiment, the implant 210 is coupled to the portions of the delivery members 230 and 250 by sliding the portions of the delivery members 230 and 250 into the slots defined by the coupling members 220 and 240 of the implant 210.

Figure 7:
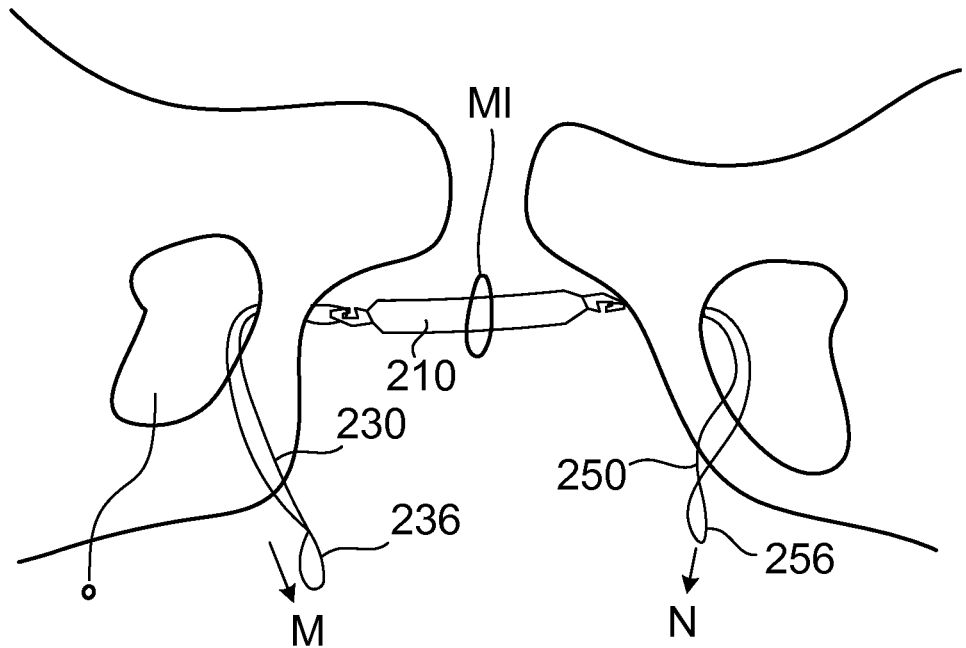

As illustrated in FIG. 7, once the implant 210 is coupled to the delivery members 230 and 250, the implant 210 may be advanced or moved into place within the body of the patient. In the illustrated embodiment, the implant 210 may be advanced or placed within the body of the patient by moving end portions 236 and 256 of the delivery members 230 and 250, respectively, in directions away from the body of the patient (such as in the directions of arrows M and N). The implant 210 can be inserted into the body via the vaginal midline incision MI and may be appropriately placed within the body. For example, in some embodiments, the implant 210 is placed to provide support to the urethra, the bladder neck, or the bladder of a patient. In such embodiments, the implant 210 is disposed adjacent to such bodily structure. In other embodiments, the implant 210 is configured to be disposed adjacent to and provide support to another portion of the body of the patient.

In some embodiments, the delivery members 230 and 250 can be used to tension the implant 210 within the body of the patient at a time after the procedure to place the implant 210 has been completed. For example, the delivery members 230 and 250 can be taped to an outer surface of the skin of the patient. A few hours or days after the procedure (for example, after the midline incision MI is closed via stitching) to place the implant 210, a physician may apply pressure (pull) to the delivery members 230 and 250 to apply additional tension to the implant 210.

Figure 8:
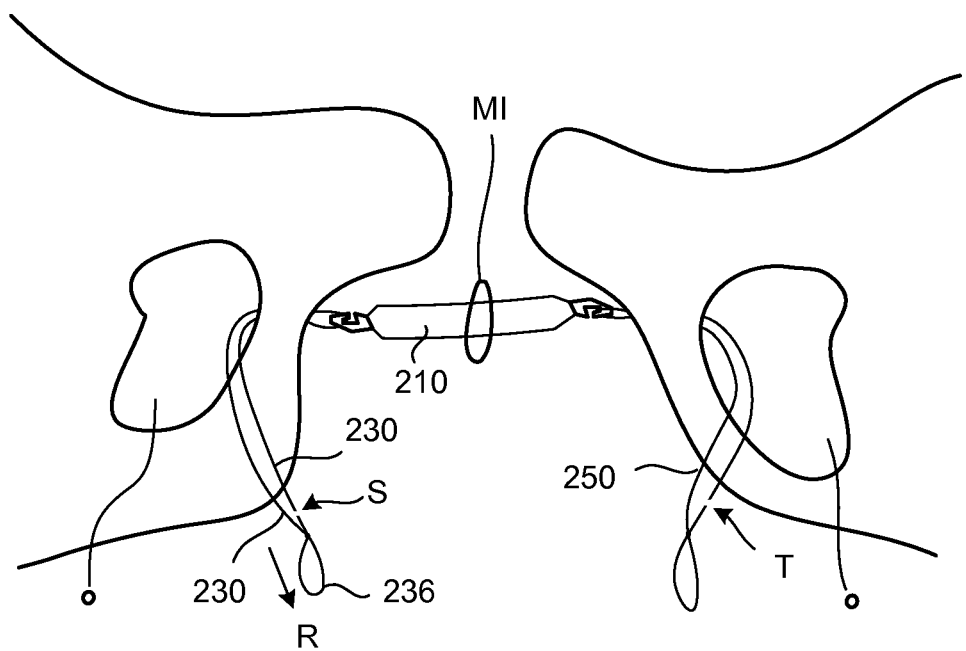

As illustrated in FIG. 8, the loop portions of the delivery members 230 and 250 may be cut. Specifically, one portion or strand of each of the loop portions of the delivery members 230 and 250 is cut. For example, delivery member 230 may be cut at location S and delivery member 250 may be cut at location T. The delivery members 230 and 250 may then be pulled in directions away from the body of the patent to remove the delivery members 230 and 250 from the implant 210. Specifically, for example, end portion 236 of the delivery member 230 may be pulled in the direction of arrow R. The delivery member 230 may be grasped and pulled with a hand or with a hemostat. Accordingly, as the delivery member 230 is slideably coupled to the implant 210, the cut portion of the delivery member 230 will travel towards the implant 210 and through the slot defined by the coupling member of the implant 210 to release or decouple the delivery member 230 from the implant 210. The releasing or decoupling of the delivery member 230 from the implant 210 occurs while the coupling member of the implant 210 is disposed within the body of the patient. For example, in some embodiments, the delivery member 230 is decoupled from the implant 210 while the implant 210 is entirely disposed within the body of the patient.

In some embodiments, the physician may choose to not remove or decouple the delivery members 230 and 250 from the implant 210. In such cases, the delivery members 230 and 250 may be tucked beneath the skin near the skin incision.

Figure 9:
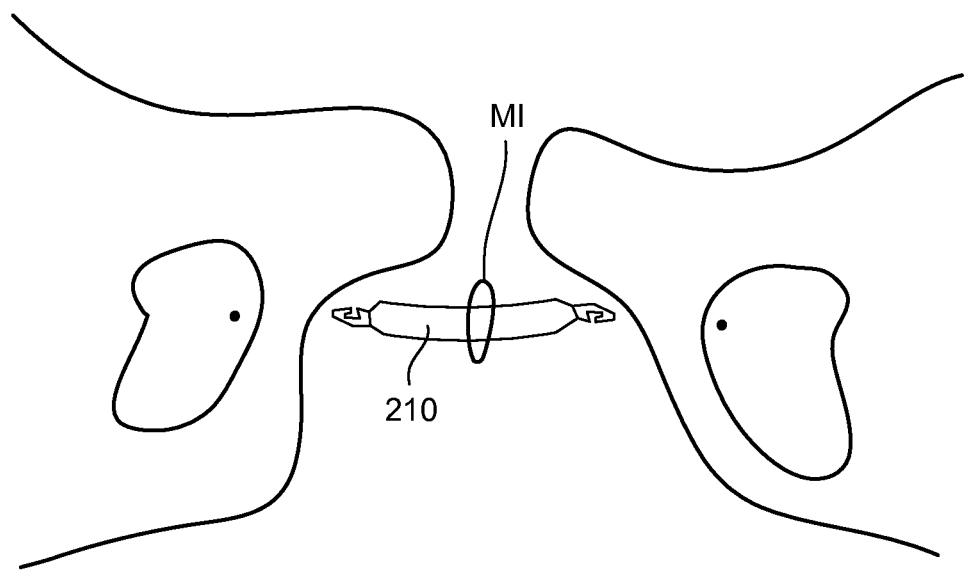

As illustrated in FIG. 9, once the delivery members 230 and 250 are removed from the implant 210, the implant 210 remains in place within the body of the patient. As discussed above, the implant 210 can be of any length. Thus, the implant 210, once placed within the body of the patient, may span to different locations within the body. For example, in some embodiments, the implant 210 extends from one obturator foramen to another obturator foramen.

FIGS. 10, 10A, and 11-17 illustrate different embodiments of the delivery member. In all of these embodiments, the delivery members may be cut at a location, such as location D, to facilitate the removal or decoupling of the delivery member from implant.

Figure 10:
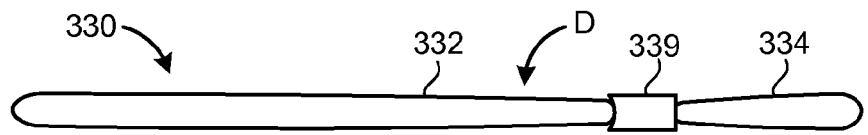
FIGS. 10, 10A, and 11-17 illustrate delivery members according to different embodiments of the invention.
Figure 10A:
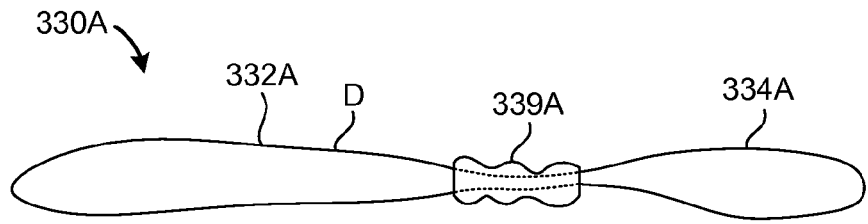

In FIG. 10, the delivery member 330 includes a first elongate portion 332 and a second elongate portion 334. The delivery member 330 also includes a crimp 339 that is coupled to the first elongate portion 332 and to the second elongate portion 334. In FIG. 10A, the delivery member 330A includes a first elongate portion 332A and a second elongate portion 334A. The delivery member 330A also includes a coupling member 339A that is coupled to the first elongate portion 332A and to the second elongate portion 334A. The coupling member 339A may be a heat shrink tube that has been coupled to the first elongate portion 332A and to the second elongate portion 334A. In some embodiments, a portion of the heat shrink tube is removed from the delivery member 330A. For example, the excess material of the heat shrink tube may be cut or peeled off of the delivery member 330A. In some embodiments, the entire heat shrink tube remains coupled to the elongate portions 330A and 332A. In other embodiments, another type of coupling member or material, such as an adhesive, is used to couple the first elongate portion to the second elongate portion.

Figure 11:
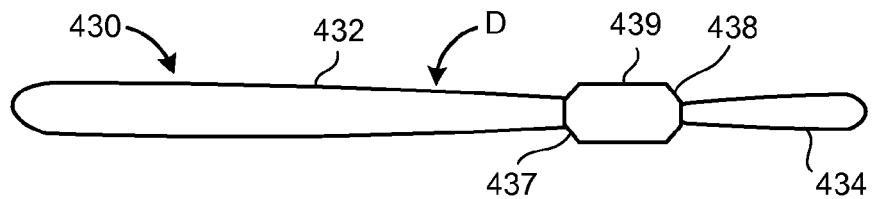

In FIG. 11, the delivery member 430 includes a dilator 439 that includes tapered portions 437 and 438. The dilator is coupled to the first elongate portion 432 and to the second elongate portion 434 and is configured to dilate the bodily tissue as the delivery member 430 or the implant is placed within the body of the patient. In some embodiments, the dilator 439 is a molded member and can be of any size.

Figure 12:
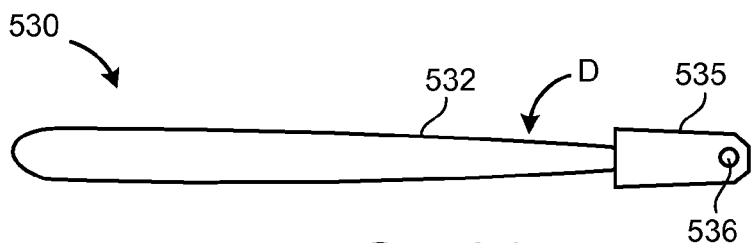
Figure 13:
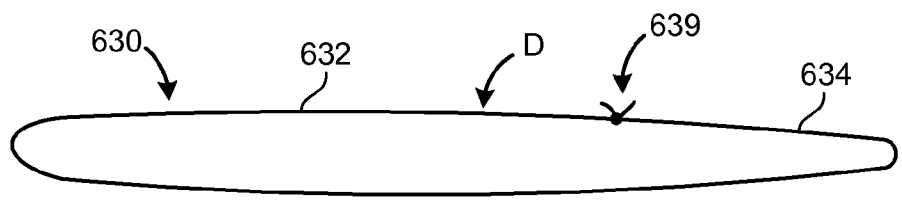

In FIG. 12, the delivery member 530 includes an elongate portion 532 coupled to a coupling member 535. The elongate portion 532 forms a loop. The coupling member 535 defines an opening 536 and is configured to be coupled to a delivery tool. In some embodiments, the coupling member 535 is configured to dilate bodily tissue as the delivery member is inserted into the body of the patient. In FIG. 13, the delivery member 630 includes a loop having a first elongate portion 632 and a second elongate portion 634. The loop is formed by tying ends of the delivery member 630 together in a knot 639. If the loop is cut on the other side of the knot 639, the knot 639 would be pulled into the body of the patient and could become tangled in the implant within the body of the patient.

Figure 14:
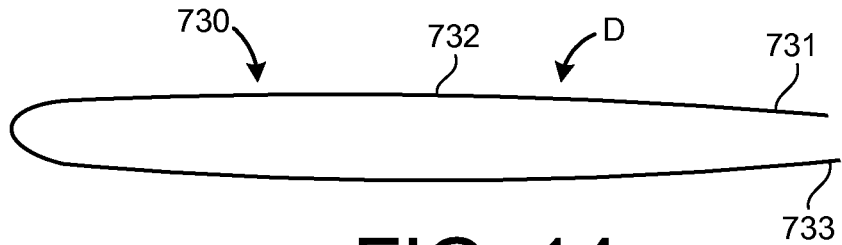
Figure 15:
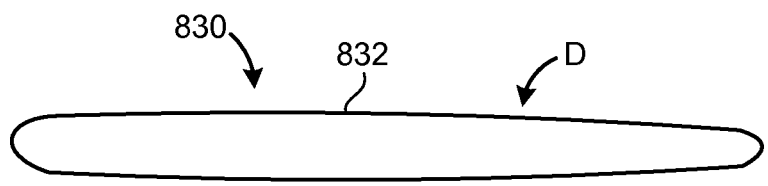

In FIG. 14, the delivery member 730 includes an elongate portion 732. The delivery member 730 includes a pair of free ends 731 and 733. In this embodiment, it may not be necessary to cut the delivery member 730 to remove the delivery member from the implant. In FIG. 15, the delivery member 830 forms a loop and includes an elongate portion 832. In some embodiments, the loop is monolithically formed as a loop. In other embodiments, ends of the elongate portion are coupled or fused together to form the loop.

Figure 16:
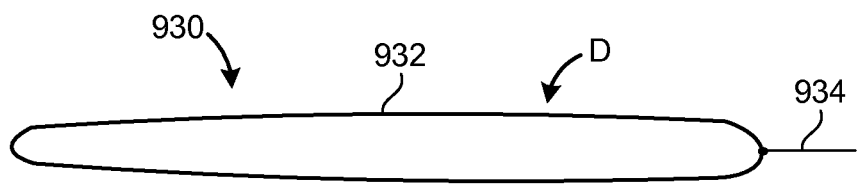

In FIG. 16, the delivery member 930 includes a first elongate portion 932 and a second elongate portion 934. The first elongate portion 932 is coupled to the second elongate portion 934. The first elongate portion 932 defines a loop. The second elongate portion 943 is a single strand that is configured to be associated with a delivery tool. In some embodiments, the single strand may be used to couple the delivery member 930 to a delivery tool that has a very small coupling portion or eyelet. In some embodiments, the second elongate portion 943 is multiple strands that do not form a loop.

Figure 17:
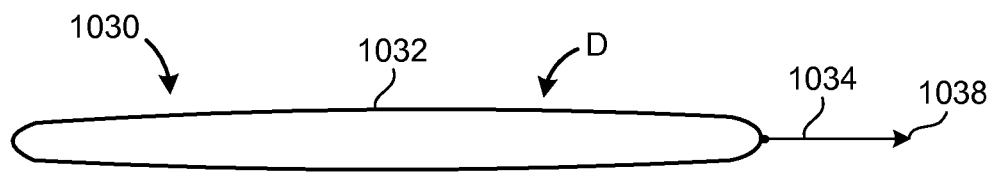

In FIG. 17, the delivery member 1030 includes a first elongate portion 1032 and a second elongate portion 1034. The delivery member 1030 includes a needle 1038 coupled to an end portion of the second elongate member 1034. The needle 1038 may includes a tissue piercing tip and may be configured to engage a delivery tool to couple the delivery member to the delivery tool (such as a Capio® device as sold by Boston Scientific Corporation).

In other embodiments, the delivery member may be coupled to a guidewire for placement within the body of the patient. For example, in some embodiments, the guidewire may be about 5 to 8 inches long and may include a tissue penetrating tip.

FIGS. 18A-18L illustrate various delivery tools coupled to various delivery members.

Figure 18A:
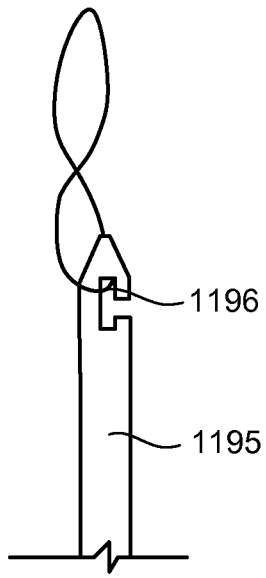
FIGS. 18A-18L illustrate delivery members coupled to delivery tools according to different embodiments of the invention.
Figure 18B:
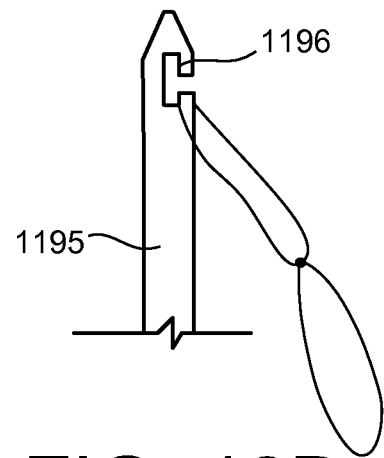
Figure 18C:
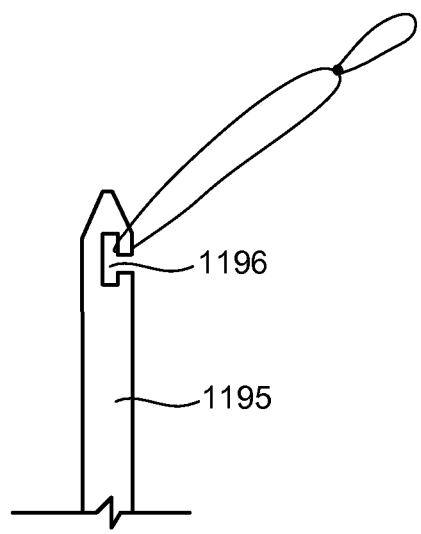

FIGS. 18A-18C illustrate a delivery tool 1195 that defines or includes a T shaped slot 1196. The T shaped slot 1196 may be used to couple the delivery tool 1195 to a delivery member and place the delivery member into the body of the patient by "carrying" the delivery member into place within the body of the patient or by "pulling" the delivery member into place within the body of the patient. "Carrying" the delivery member into place occurs when the delivery member is coupled to the delivery tool before the delivery tool is inserted into the body of the patient. "Pulling" the delivery member into place occurs when the delivery member is coupled to the delivery tool before the delivery tool is inserted into the body of the patient.

Figure 18D:
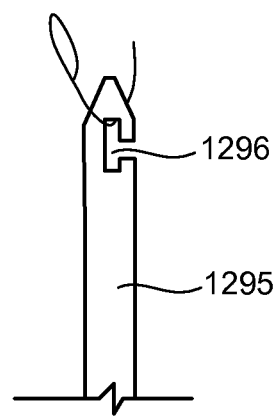
Figure 18E:
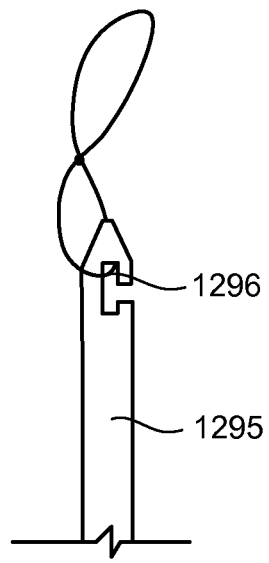
Figure 18F:
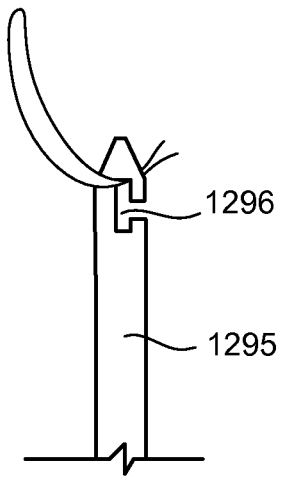

FIGS. 18D-18F illustrate a delivery tool 1295 that defines or includes an L shaped slot 1296. The L shaped slot 1296 may be used to couple the delivery tool 1295 to a delivery member and place the delivery member into the body of the patient by pulling the delivery member into place within the body of the patient.

Figure 18G:
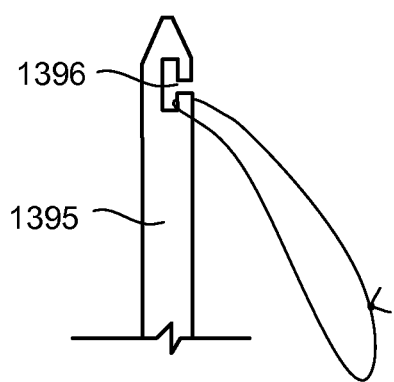
Figure 18H:
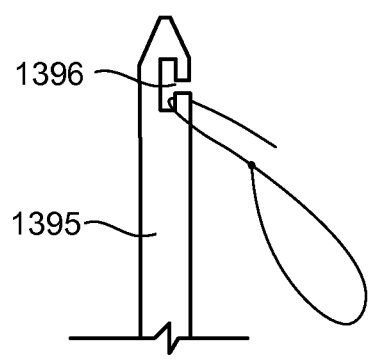
Figure 18I:
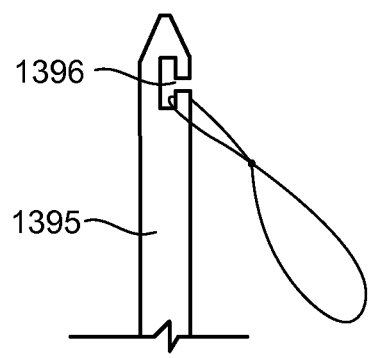

FIGS. 18G-18I illustrate a delivery tool 1395 that defines or includes a reverse L shaped slot 1396. The reverse L shaped slot 1396 may be used to couple the delivery tool 1395 to a delivery member and place the delivery member into the body of the patient by carrying the delivery member into place within the body of the patient.

Figure 18J:
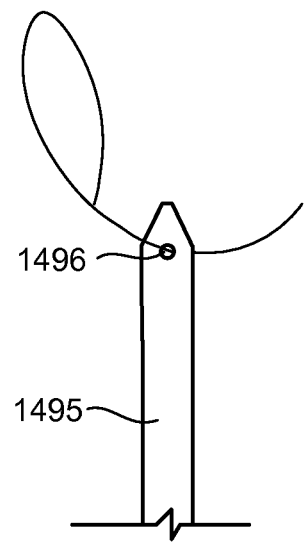
Figure 18K:
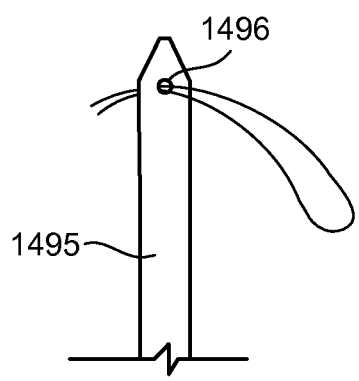
Figure 18L:
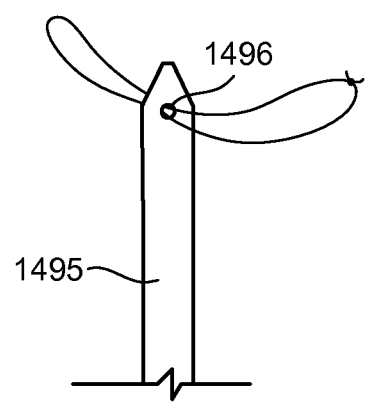

FIGS. 18J-18L illustrate a delivery tool 1495 that defines or includes an opening 1496. The opening 1496 may be used to couple the delivery tool 1495 to a delivery member and place the delivery member into the body of the patient by carrying the delivery member into place within the body of the patient or by pulling the delivery member into place within the body of the patient.

Figure 19A:
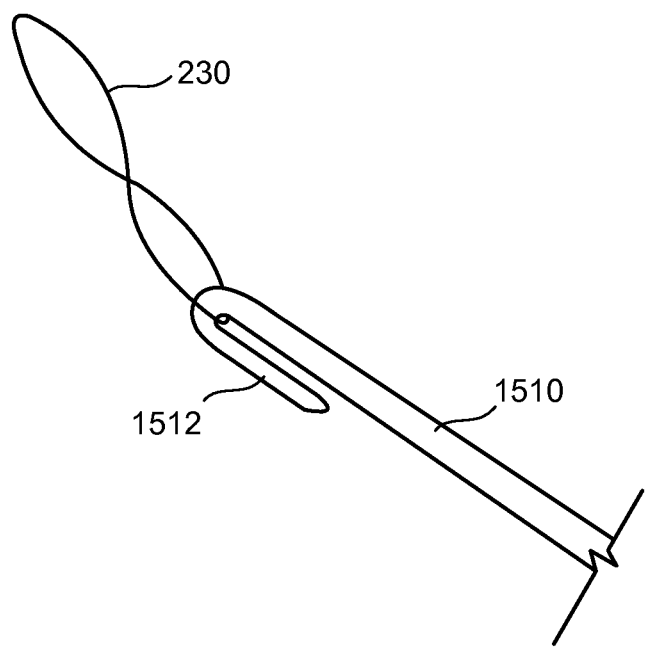
FIGS. 19A and 19B illustrate implants according to different embodiments of the invention.
Figure 19B:
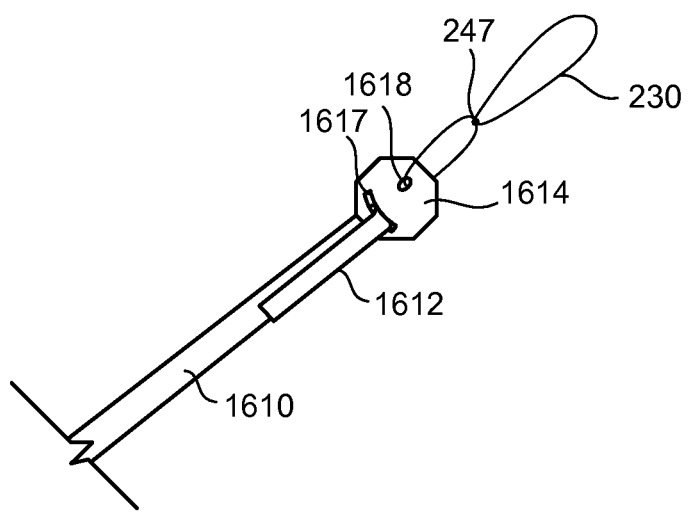

FIGS. 19A and 19B illustrate an adjustable length implant. As illustrated in FIG. 19A, the implant 1510 includes a folded portion 1512. The delivery member 230 is coupled to the implant 1510 at the folded portion 1512. Any excess implant material may be removed from the implant 1510. As illustrated in FIG. 19B, the implant 1610 includes a folded portion 1612 and a connector 1614. The connector 1614 defines a U shaped slot 1617 configured to receive a portion of the implant 1610 to slidably couple the implant 1610 to the connector 1614. The connector 1614 also defines an opening 1618 configured to couple the implant 1610 to the delivery member 230. In some embodiments, the delivery member 230 includes a dilator 247 configured to dilate the bodily tissue as the implant 1610 is delivered to the body.

Figure 20:
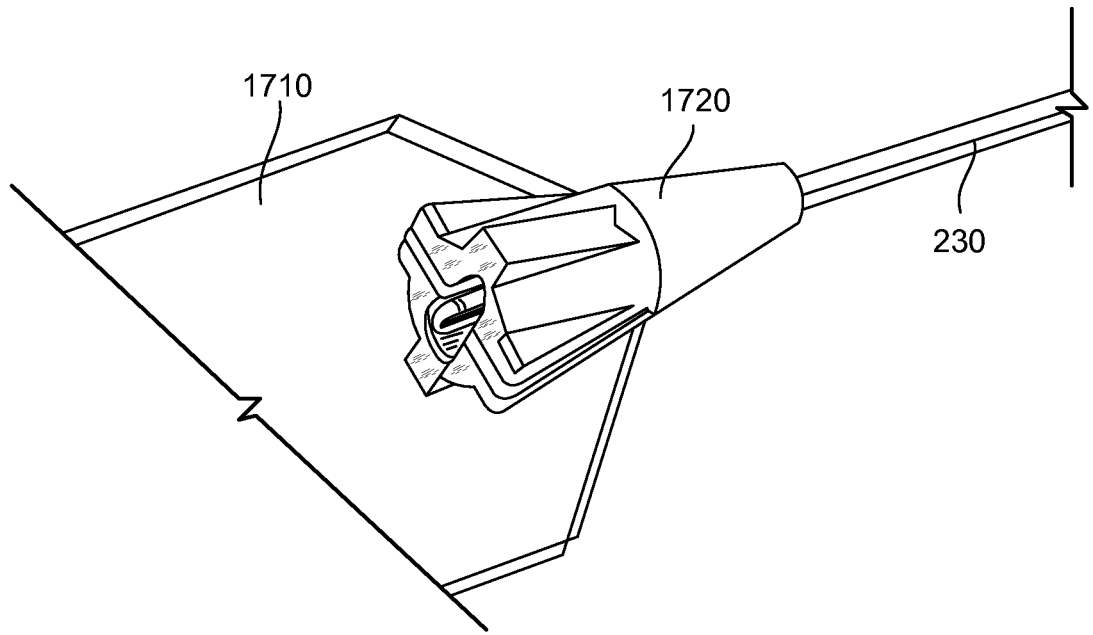
FIG. 20 illustrates a portion of an implant according to an embodiment of the invention.

FIG. 20 illustrates an implant 1710 that is coupled to the delivery member 230 before the delivery member 230 is inserted into the body of the patient. For example, the delivery member 230 may be coupled to the implant 1710 during the manufacturing of the implant 1710. In other words, the implant 1710 and the delivery member 230 are pre-assembled by the manufacture. In the illustrated embodiment, the delivery member 230 is threaded through a lumen defined by the connector 1720 and may also be threaded through the implant 1710. The delivery member 230 may be inserted into the body of the patient via an outside-in approach or an inside-out approach. Once the delivery members have been placed within the body of the patient, the delivery members may be used to delivery and place the implant 1710 into the body of the patient.

Figure 21:
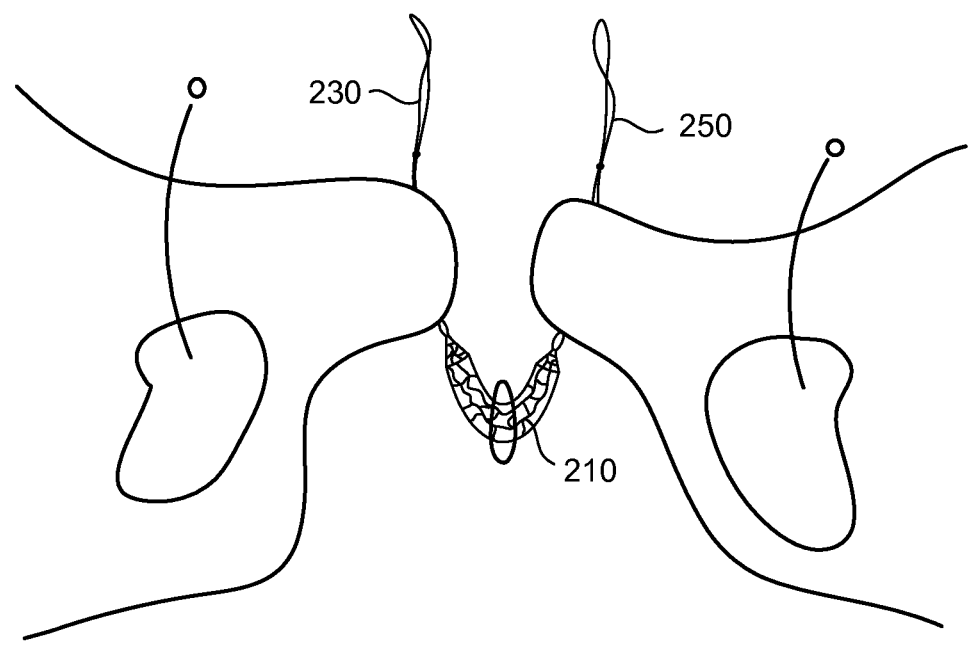
FIGS. 21-23 schematically illustrate embodiments of an implant (or portions of a medical device) disposed within a body of a patient.

FIG. 21 is a schematic illustration of an implant disposed within a body of a patient. In this embodiment, the implant 210 has been placed using a retropubic or a suprapubic approach. Specifically, the delivery members 230 and 250 do not extend through the obturators. Rather, the delivery members 230 and 250 extend toward and out the abdomen of the patient.

Figure 22:
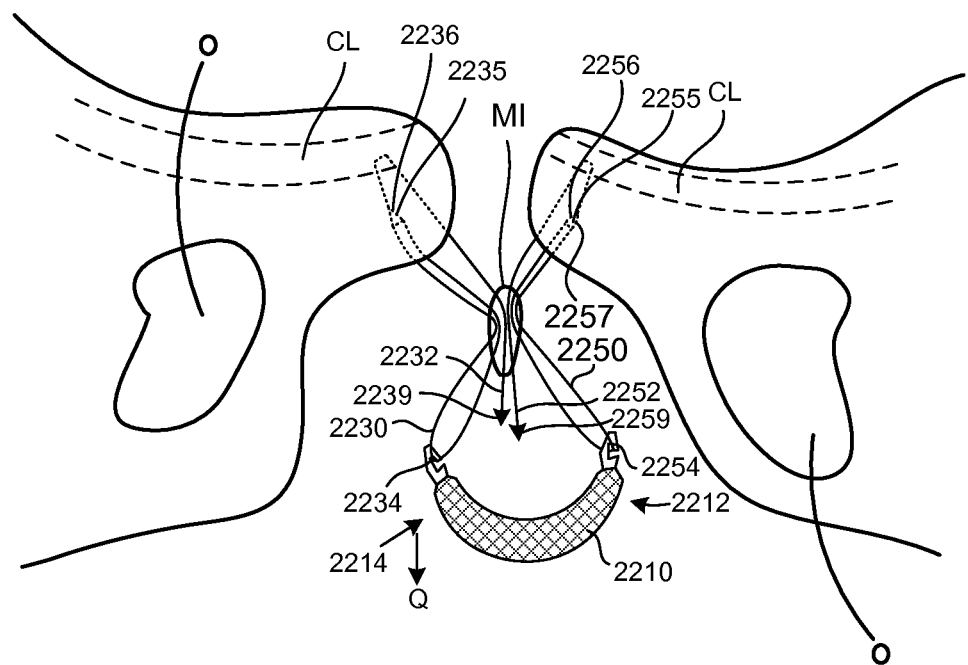

FIG. 22 is a schematic illustrate of an implant 2210 and delivery members 2230 and 2250 disposed within a body of a patient. The delivery members 2230 and 2250 are disposed through and coupled to the Cooper's ligaments CL of the patient. In some embodiments, a suturing or insertion tool may be used to pass the delivery members 2230 into the pelvic region via the midline incision MI and 2250 through the Cooper's ligaments CL. For example, in some embodiments, a Capio® device, as sold by Boston Scientific Corporation, may be used to delivery the delivery members 2230 and 2250 through the Cooper's ligaments CL. In the illustrated embodiment, the distal end portions 2232 and 2252 of the delivery members, respectively, include dart needles 2239 and 2259. The dart needles 2239 and 2259 are configured to be coupled to a suturing or insertion tool.

As illustrated, the proximal end portions 2234 and 2254 of the delivery members 2230 and 2250, respectively, are coupled to the implant 2210. In the illustrated embodiment, the implant 2210 does not include any coupling members. Rather the delivery members 2230 and 2250 are coupled directly to the implant 2210. In the illustrated embodiment, the implant 2210 is formed of a mesh material and the delivery members 2230 and 2250 are treaded through the mesh material to couple the delivery members 2230 and 2250 to the implant 2210.

To deliver the implant 2210 into the body of the patient, the delivery members 2230 and 2250 may be disposed within the body of the patient such that the distal end portions 2232 and 2252 of the delivery members 2230 and 2250, respectively, extend from the midline incision MI. The delivery members 2230 and 2250 may then be pulled in the direction of Q to place the implant 2210 into the body of the patient. In the illustrated embodiment, the implant 2210 includes tanged portions 2212 and 2214 that are configured to help retain the implant 2210 in place within the body of the patient. For example the tanged portions 2212 and 2214 of the implant 2210 may extend through and couple to the Cooper's ligaments CL.

Once the implant 2210 is disposed within the body of the patient, a portion of the loops of the delivery members 2230 and 2250 may be cut and pulled to decouple or remove the delivery members 2230 from the implant 2210 (leaving the implant 2210 in place within the body). In some embodiments, the delivery members 2230 and 2250 may be left extended from the midline incision MI for adjustment of the tension or placement of the implant within the body at a time after the procedure to place the implant within the body of the patient.

In the illustrated embodiment, the delivery members 2230 and 2250 are each coupled to or include a dilator 2235 and 2255. The dilators 2235 and 2255 may be of any shape or size and are configured to dilate the bodily tissue prior to insertion of the implant 2210 through the bodily tissue. In the illustrated embodiment, dilator 2235 includes a first tapered portion 2236. In the illustrated embodiment, dilator 2255 includes a first tapered portion 2256 and a second tapered portion 2257.

In one embodiment, after the implant 2210 has been placed within the body of the patient, the distal end portions 2232 and 2252 of the delivery members 2230 and 2250 are knotted or coupled together and left disposed within the body of the patient.

In other embodiments, the delivery members 2230 and 2250 are not placed through the Cooper's ligament CL, rather the delivery members 2230 and 2250 are placed through other bodily or pelvic tissue.

Figure 23:
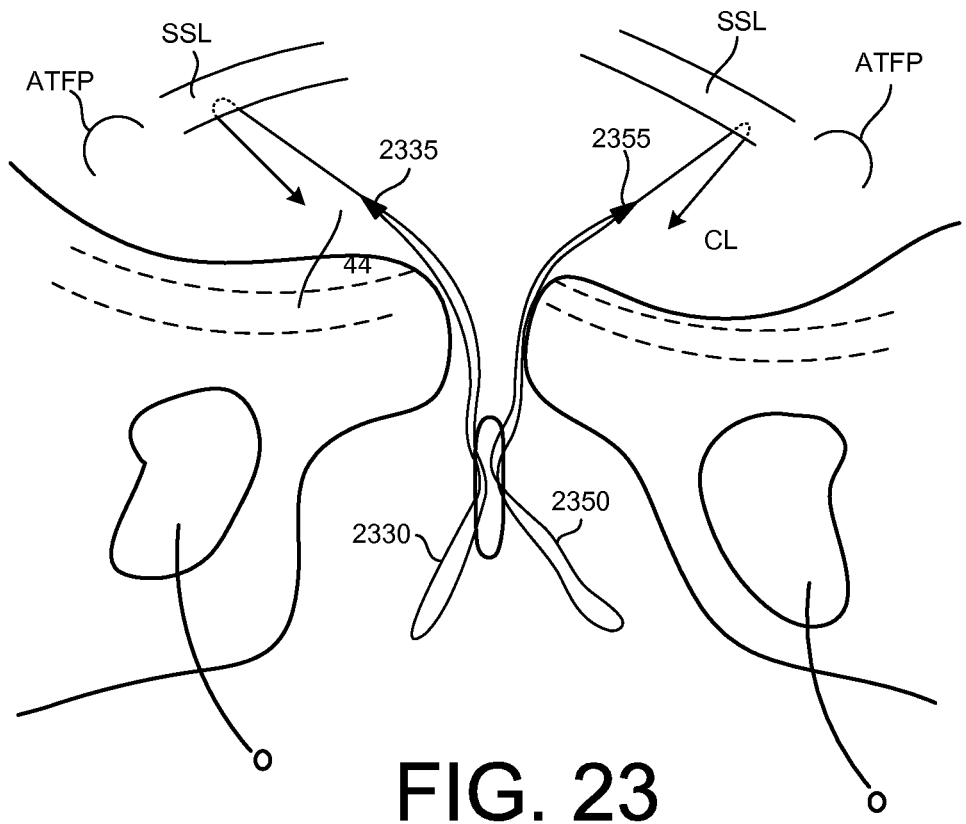

As illustrated in FIG. 23, delivery members 2330 and 2350 are inserted through the midline incision MI and through the sacrospinous ligaments SSL of the patient. For example, in some embodiments, a suturing or insertion tool can be used to place the delivery members 2330 and 2350 though the sacrospinous ligaments SSL. In the illustrated embodiment, the delivery members 2330 and 2350 include dilators 2335 and 2355. In some embodiments, the delivery members 2330 and 2350 are color coded (or of different colors) to identify the correct side of the patient that should receive the different delivery members 2330 and 2350. Once the delivery members 2330 and 2350 are placed within the body of the patient, an implant can be coupled to the members and inserted into the body as described above. In some embodiments, the implant extends through the sacrospinous ligaments SSL to couple the implant within the body of the patient.

In some embodiments, the implant may be inserted into the body of the patient with more than two delivery members. For example, in some embodiments, the implant includes four, six or more arms or coupling portions and a delivery member is inserted for each arm or coupling portion.

In some embodiments, the implant includes coupling members configured to couple to the delivery members. In some embodiments, the coupling members remain implanted within the body of the patient. In other embodiments, the coupling members are removed from the implant prior to closing the midline incision.

In some embodiments, the delivery members extend through and the implant is coupled to different portions of the pelvic region. For example, in some embodiments, the delivery members extend through the arcus tendious facia pelvis of the patient ATFP.

Figure 24:
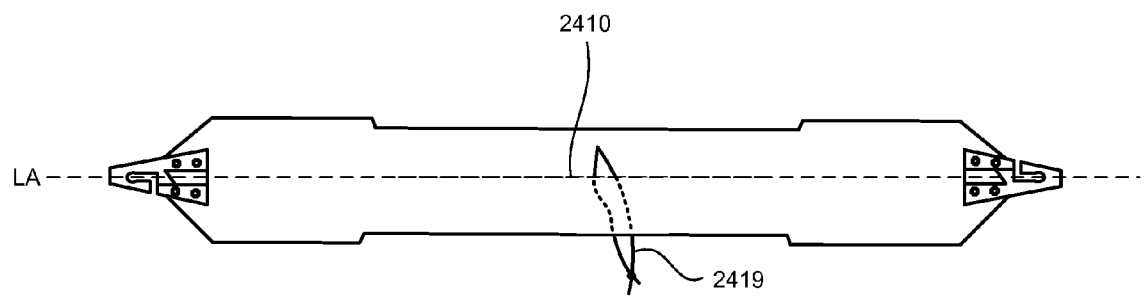
FIG. 24 illustrates an implant according to an embodiment of the invention.

As illustrated in FIG. 24, in some embodiments, the implant 2410 includes an adjustment or center loop 2419. The center loop 2419 may be extend from the midine incision and may be used to adjust the tension (loosen the tension) of the implant 2410 either during or after the procedure to place the implant within the body of the patient. For example, in some embodiments, the after the procedure to place the implant within the body of the patient, the center loop 2419 is left extending from the incision. Thus, for a period of time after the procedure to place the implant 2410, the center loop 2419 may be used to loosen or adjust the tension of the implant 2410 within the body of the patient. Once the implant 2410 is properly placed and tensioned, the center loop 2419 may be cut and removed from the implant 2410.

In some embodiments, the adjustment or center loop 2419 is formed of a filament that is configured to absorb fluids. For example, in some embodiments, the adjustment or center loop 2419 is configured to absorb and deliver medications to prevent infections to the body of the patient.

In the illustrated embodiment, the center loop 2419 is a thread or thread-like member and is threaded through the implant 2410 with the ends of the center loop 2419 knotted or crimped together. In the illustrated embodiment, the center loop 2419 extends in a direction substantially perpendicular to the longitudinal axis LA of the implant 2410. In other embodiments, the center loop 2419 extends in a different direction with respect to the longitudinal axis LA of the implant 2410.

In some embodiments, to remove the center loop 2419 from the implant 2410, one portion of the loop is cut, the knot or crimp is grasped, and pulled away from the implant 2410. Accordingly, the knot or crimp does not get tangled with the implant 2410.

Figure 25:
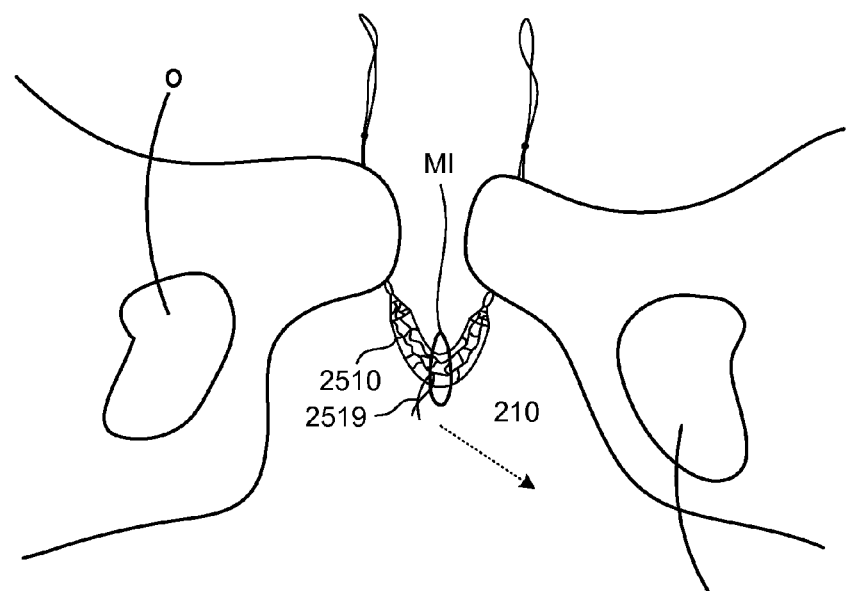
FIG. 25 schematically illustrates an embodiment of an implant disposed within a body of a patient.

FIG. 25 schematically illustrates an implant 2510 disposed within a body of a patient. As illustrated, the adjustment loop 2519 is biased or disposed closer to one end of the implant 2510. Accordingly, pulling the loop in the direction of arrow G (either during the procedure to place the implant or at a time after the procedure to place the implant) loosens the tension of the implant 2510 within the body of the patient.

Figure 26:
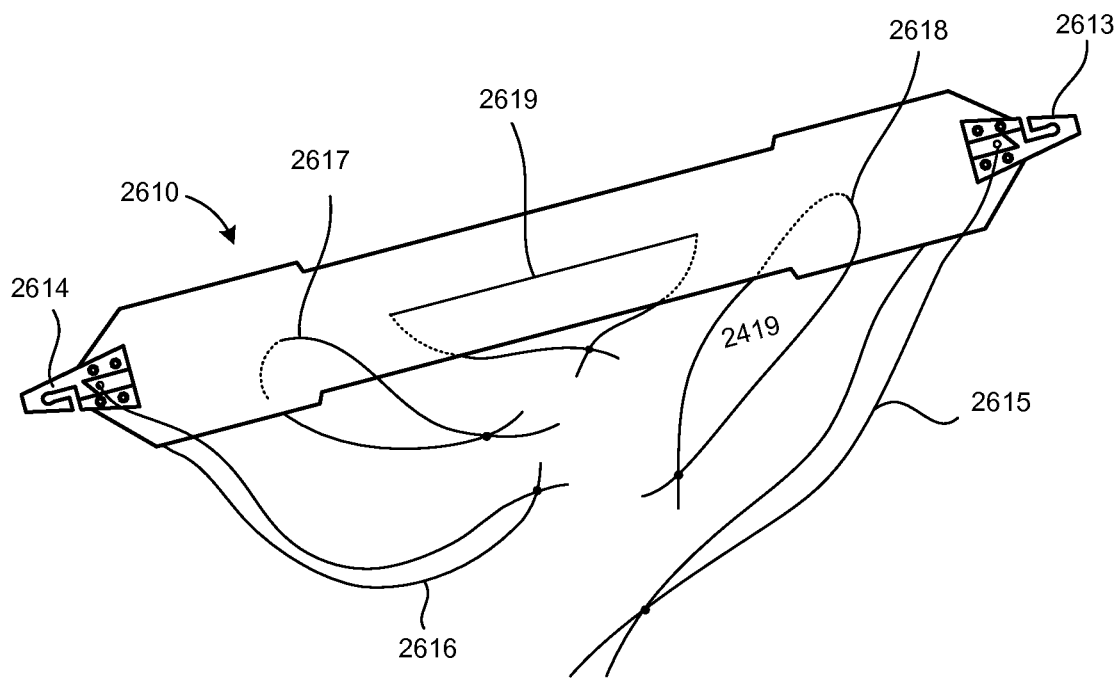
FIG. 26 illustrates an implant according to an embodiment of the invention.

Any number of adjustment loops may be coupled to the implant. For example, as illustrated in FIG. 26, the implant 2610 may have five adjustment loops 2619, 2618, 2617, 2616, and 2615. In the illustrated embodiment, the adjustment loop 2619 is coupled near the middle of the implant 2610 and adjustment loops 2618 and 2617 are coupled to the implant 2610 closer to the ends of the implant 2610. Adjustment loops 2616 and 2615 are coupled near the end portions of the implant 2610. Specifically, adjustment loops 2616 and 2615 are coupled or threaded through the coupling members 2614 and 2613 of the implant 2610, respectively. Any combination of adjustment loops may be used. Accordingly, pressure or pulling of the different adjustment loops provide or adjust the tension of the implant in different locations.

Figure 27:
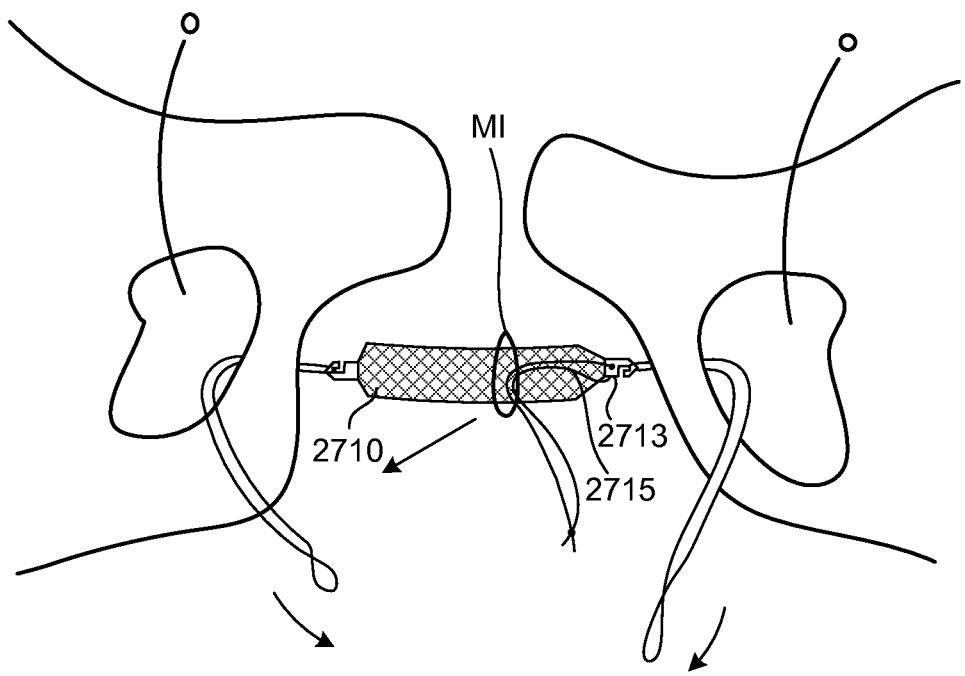
FIG. 27 schematically illustrates an embodiment of an implant disposed within a body of a patient.

FIG. 27 schematically illustrates an implant 2710 disposed within a body of a patient. In the illustrated embodiment, the adjustment loop 2715 is coupled to the coupling member 2713 and extends from the midline incision MI. Accordingly, the adjustment loop 2715 may be pulled in the direction of arrow J to move an end portion of the implant with respect to the body of the patient loosen the tension of the implant 2710 within the body of the patient.

Figure 28:
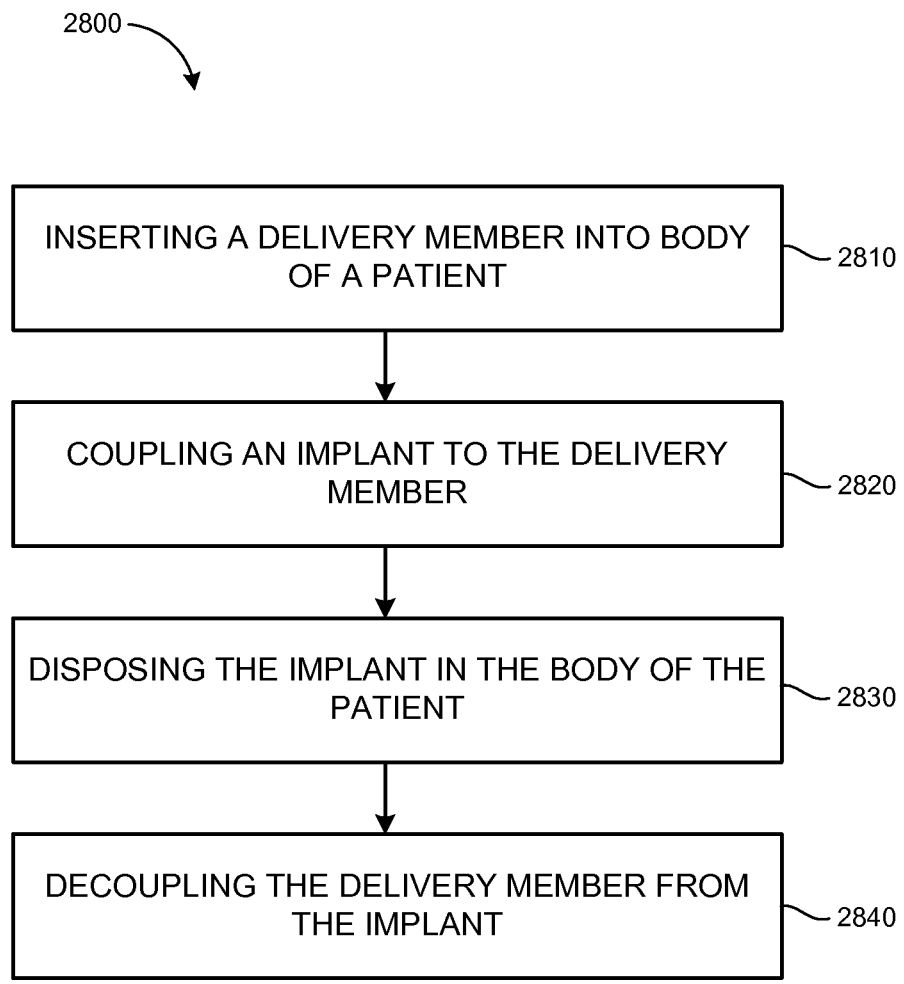
FIG. 28 is a flow chart illustrating a method of placing an implant within a body of a patient according to an embodiment of the invention.

FIG. 28 illustrates a method 2800 of inserting an implant within a body of a patient. At 2810, a delivery member is inserted into a body of a patient such that a first portion of the delivery member is disposed within the body of the patient and another portion of the delivery member extends from the body of the patient. In some embodiments, the delivery member is inserted into the body of the patient using a delivery tool.

In some embodiments, the method includes creating an incision, such as a vaginal midline incision. In some embodiments, the method includes creating an anterior vaginal incision and/or a posterior vaginal incision.

At 2820, once the delivery member is disposed in the body of the patient, an end portion of an implant is coupled to the delivery member. At 2830, the end portion of the implant is disposed within or inserted into the body of the patient. For example, in some embodiments, an end portion of the delivery member is pulled or moved away from the body of the patient to advance the implant into the body of the patient.

At 2840, the delivery member is decoupled or removed from the implant while the end portion of the implant is disposed within the body of the patient. In some embodiments, the delivery member is decoupled or removed from the implant by cutting a portion of a loop portion and pulling the delivery member away from the implant or body of the patient.

In some embodiments, a medical device includes a first elongate portion and a second elongate portion. The first elongate portion defines a loop. The first elongate portion has a first end portion and a second end portion. The first end portion is configured to be removably coupled to an implant. The second elongate portion has a first end portion and a second end portion. The first end portion of the second elongate portion is coupled to the first elongate portion. The second end portion of the second elongate portion is configured to be removably coupled to an insertion tool.

In some embodiments, a knot is disposed between the first elongate portion and the second elongate portion. In some embodiments, a coupler is disposed between the first elongate portion and the second elongate portion. The coupler has a first end portion coupled to the first elongate portion and a second end portion coupled to the second elongate portion.

In some embodiments, a dilator is disposed between the first elongate portion and the second elongate portion. The dilator has a first end portion coupled to the first elongate portion and a second end portion coupled to the second elongate portion. The dilator has a tapered portion.

In some embodiments, the second elongate portion includes a loop. In some embodiments, the second elongate portion includes a loop. The loop is configured to engage a slot defined by the insertion tool to removably couple the second elongate portion to the insertion tool.

In some embodiments, a kit includes an implant, a first delivery member, and a second delivery member. The implant is configured to be placed within a body of a patient. The implant has a first end portion and second end portion. The first delivery member has a first elongate portion and a second elongate portion. The first elongate portion includes a loop and being configured to be coupled to the first end portion of the implant. The second delivery member has a first elongate portion and a second elongate portion. The first elongate portion includes a loop and being configured to be coupled to the second end portion of the implant.

In some embodiments, the implant includes a support member and a coupling member. The coupling member includes a coupling portion configured to be removably coupled to the first delivery member.

In some embodiments, the implant includes a support member and a coupling member. The coupling member defines a slot configured to receive a portion of the first elongate portion to removably couple the first elongate portion to the implant. In some embodiments, the implant includes a support member and a coupling member. The coupling member defines a slot configured to receive a portion of the first elongate portion to removably couple the first elongate portion to the implant. The slot has a first portion extending along a first axis and a second portion extending along a second axis. The first axis being non-parallel to the second axis.

In some embodiments, the second elongate portion of the first delivery member includes a loop.

In some embodiments, a method of inserting an implant within a body of a patient includes (a) inserting a delivery member into the body of the patient such that a first portion of the delivery member is disposed within the body of the patient and a second portion of the delivery member extends from the body of the patient; (b) coupling the second portion of the delivery member to an end portion of the implant after the inserting of the delivery member; (c) disposing the end portion of the implant within the body of the patient; and (d) decoupling the second portion of the delivery member from the end portion of the implant while the end portion of the implant is disposed within the body of the patient.

In some embodiments, the coupling the second portion of the delivery member to an end portion of the implant includes engaging the second portion of the delivery member with a slot defined by a coupler of the implant.

In some embodiments, the second portion of the delivery member includes a loop portion. The coupling the second portion of the delivery member to an end portion of the implant includes engaging the loop portion of the second portion of the delivery member with a slot defined by a coupler of the implant.

In some embodiments, the inserting a delivery member into the body of the patient includes associating the first portion of the delivery member with an insertion tool and advancing the delivery member into the body of the patient.

In some embodiments, the first portion of the delivery member includes a loop portion. The inserting a delivery member into the body of the patient includes associating the loop portion of the first portion of the delivery member with an insertion tool and advancing the delivery member into the body of the patient.

In some embodiments, the second portion of the delivery member extends from the body of the patient at a first location. The inserting a delivery member into the body of the patient includes inserting the delivery member into the body of the patient such that a third portion of the delivery member extends from the body of the patient at a second location different than the first location.

In some embodiments, the second portion of the delivery member extends from a vaginal incision. The inserting a delivery member into the body of the patient includes inserting the delivery member into the body of the patient such that a third portion of the delivery member extends from a secondary skin incision proximate an obturator foramen of the patient.

In some embodiments, the second portion of the delivery member includes a loop portion. The decoupling the second portion of the delivery member from the end portion of the implant includes cutting a portion of the loop portion of the delivery member and moving the first portion of the delivery member in a direction away from the implant.

In some embodiments, the method includes (1) inserting a second delivery member into the body of the patient such that a first portion of the second delivery member is disposed within the body of the patient and a second portion of the second delivery member extends from the body of the patient; (2) coupling the second portion of the second delivery member to a second end portion of the implant after the inserting of the second delivery member; (3) disposing the second end portion of the implant within the body of the patient; and (4) decoupling the second portion of the second delivery member from the second end portion of the implant while the second end portion of the implant is disposed within the body of the patient.

While certain features of the described implementations have been illustrated as described herein, many modifications, substitutions, changes and equivalents will now occur to those skilled in the art. For example, although the procedures above have focused on placing a device within a female patient, the apparatuses and methods disclosed herein may be used on male patients. It is, therefore, to be understood that the appended claims are intended to cover all such modifications and changes as fall within the scope of the embodiments.

What is claimed is:

1. A medical device, comprising:
   an implant having a mesh material, the implant having an end portion;
   a coupling component coupled to the end portion of the implant, the coupling component defining a slot, the slot including a first portion extending along a first axis and a second portion extending along a second axis, the second axis being disposed at a non-zero angle with respect to the first axis, the slot defining an opening on a lateral edge of the coupling component;
   a first elongate portion defining a first loop, the first loop at least partially formed by a suture, the first elongate portion having a first end portion and a second end portion, the first end portion being configured to be removably coupled to the slot of the implant such that a portion of the first loop can be inserted into and removed from the first portion of the slot via the opening and the second portion of the slot;

a second elongate portion defining a second loop, the second loop at least partially formed by the suture, the second elongate portion having a first end portion and a second end portion, the first end portion of the second elongate portion being coupled to the first elongate portion, the second end portion of the second elongate portion being configured to be removably coupled to an insertion tool, the first loop being longer than the second loop; and a coupling member fixedly disposed between the first elongate portion and the second elongate portion, the first loop being coupled to the second loop via the coupling member, the first loop being disposed distally from the second loop.

2. The medical device of claim 1, wherein the coupling component includes two pieces that are coupled together, the end portion of the implant being disposed between the two pieces.

3. The medical device of claim 1, wherein the coupling member includes a dilator having a first end portion coupled to the first elongate portion and a second end portion coupled to the second elongate portion, the second end portion being opposite to the first end portion along a longitudinal axis of the dilator, the dilator having a first tapered portion at the first end portion of the dilator such that the first tapered portion tapers in a direction towards the first elongate portion, the dilator having a second tapered portion at the second end portion of the dilator such that the second tapered portion tapers in a direction towards the second elongate portion.

4. The medical device of claim 1, wherein the second loop is configured to engage a T-shaped slot defined by the insertion tool to removably couple the second elongate portion to the insertion tool.

5. The medical device of claim 1, wherein the suture includes at least one strand of fiber, the at least one strand of fiber defining the first loop of the first elongate portion and the second loop of the second elongate portion.

6. The medical device of claim 1, wherein the slot of the implant is an L-shaped slot such that the second axis is perpendicular to the first axis, the first portion of the slot having an end portion that is wider than a mid-portion of the first portion of the slot.

7. A kit, comprising:
an implant configured to be placed within a body of a patient, the implant having a first end portion and second end portion;
a first coupling component coupled to the first end portion of the implant, the first coupling component defining a first slot, the first slot having an opening on a lateral edge of the first coupling component that extends into the first coupling component;
a second coupling component coupled to the second end portion of the implant, the second coupling component defining a second slot, the second slot having an opening on a lateral edge of the second coupling component that extends into the second coupling component;
an insertion tool having a needle member defining a slot;
a first delivery member, the first delivery member being a first suture, the first delivery member having a first elongate portion and a second elongate portion, the first elongate portion including a first loop and being configured to be removably coupled to the first slot of the first coupling component via the opening of the first slot, the first loop being defined by the first suture and a coupling member, the second elongate portion including a second loop, the coupling member being fixedly disposed between the first loop and the second loop, the second loop being defined by the first suture and the coupling member, the coupling member being disposed between the first elongate portion of the first delivery member and the second elongate portion of the first delivery member, the first loop being coupled to the second loop via the coupling member, the first loop being disposed distally from the second loop, the first loop being longer than the second loop, the second loop configured to be removably coupled to the slot of the needle member; and a second delivery member, the second delivery member being a second suture separate from the first suture, the second delivery member having a first elongate portion and a second elongate portion, the first elongate portion of the second delivery member including a first loop defined at least partially by the second suture, the first loop of the first elongate portion of the second delivery device being configured to be removably coupled to the second slot of the second coupling component via the opening of the second slot, the second elongate portion of the second delivery member including a second loop defined at least partially by the second suture, the second loop of the second elongate portion of the second delivery member configured to be removably coupled to the slot of the needle member.

8. The kit of claim 7, wherein the first and second slots are L-shaped slots.

9. The kit of claim 7, wherein the first coupling component includes two pieces that are coupled together, the first end portion of the implant being disposed between the two pieces.

10. The kit of claim 7, wherein each of the first and second slots has a first portion extending along a first axis and a second portion extending along a second axis, the first axis being non-parallel to the second axis, the second portion having an end portion wider than a mid-portion of the second portion.

11. The kit of claim 7, wherein the first loop of the first elongate portion of the first delivery member is a first complete loop, and the second loop of the second elongate portion of the first delivery member includes a second complete loop.

12. A method of inserting an implant within a body of a patient, comprising:
inserting a delivery member into the body of the patient such that a first portion of the delivery member is disposed within the body of the patient and a second portion of the delivery member extends from the body of the patient, the delivery member being a suture such that the first portion of the delivery member defines a first loop and the second portion of the delivery member defines a second loop, the second loop being longer than the first loop;
coupling the second loop of the delivery member to an end portion of the implant after the inserting of the delivery member;
disposing the end portion of the implant within the body of the patient; and
decoupling the second loop of the delivery member from the end portion of the implant while the end portion of the implant is disposed within the body of the patient including cutting the second loop of the delivery member and moving the first loop of the delivery member in a direction away from the implant such that a portion of the second loop moves towards the implant and then away from the implant while the first loop of the delivery member moves in the direction away from the implant.

13. The method of claim 12, wherein the coupling the second portion of the delivery member to an end portion of the implant includes engaging the second portion of the delivery member with a slot defined by a coupler of the implant.

14. The method of claim 12, wherein the second loop of the delivery member is coupled to a slot defined by a coupler of the implant.

15. The method of claim 12, wherein the inserting a delivery member into the body of the patient includes associating the first portion of the delivery member with an insertion tool and advancing the delivery member into the body of the patient.

16. The method of claim 12, wherein the inserting a delivery member into the body of the patient includes associating the first loop of the delivery member with an insertion tool and advancing the delivery member into the body of the patient.

17. The method of claim 12, wherein the second portion of the delivery member extends from the body of the patient at a first location, the inserting a delivery member into the body of the patient includes inserting the delivery member into the body of the patient such that a third portion of the delivery member extends from the body of the patient at a second location different than the first location.

18. The method of claim 12, wherein the second portion of the delivery member extends from a vaginal incision, the inserting a delivery member into the body of the patient includes inserting the delivery member into the body of the patient such that a third portion of the delivery member extends from a secondary skin incision proximate an obturator foramen of the patient.

19. The method of claim 12, wherein the first loop is a first complete loop, and the second loop is a second complete loop, wherein the cutting includes cutting the first complete loop and the moving includes moving the second complete loop in a direction away from the implant such that a portion of the first complete loop moves towards the implant and then away from the implant while the second complete loop is moved in the direction away from the implant.

20. The method of claim 12, the delivery member being a first delivery member, the end portion of the implant being a first end portion, the method further comprising:

inserting a second delivery member into the body of the patient such that a first portion of the second delivery member is disposed within the body of the patient and a second portion of the second delivery member extends from the body of the patient;

coupling the second portion of the second delivery member to a second end portion of the implant after the inserting of the second delivery member;

disposing the second end portion of the implant within the body of the patient; and decoupling the second portion of the second delivery member from the second end portion of the implant while the second end portion of the implant is disposed within the body of the patient.

\* \* \* \* \*